US011832598B2

(12) United States Patent
Cui et al.

(10) Patent No.: US 11,832,598 B2
(45) Date of Patent: Dec. 5, 2023

(54) GENETICALLY MODIFIED NON-HUMAN ANIMALS AND METHODS FOR PRODUCING HEAVY CHAIN-ONLY ANTIBODIES

(71) Applicant: Akeagen, Inc., Irvine, CA (US)

(72) Inventors: Libin Cui, Irvine, CA (US); Xiaolin Sun, Irvine, CA (US)

(73) Assignee: AKEAGEN, INC., Irvine, CA (US)

( * ) Notice: Subject to any disclaimer, the term of this patent is extended or adjusted under 35 U.S.C. 154(b) by 666 days.

(21) Appl. No.: 16/878,362

(22) Filed: May 19, 2020

(65) Prior Publication Data

US 2020/0344983 A1   Nov. 5, 2020

Related U.S. Application Data

(60) Division of application No. 16/401,029, filed on May 1, 2019, now Pat. No. 10,660,316, which is a continuation of application No. PCT/US2017/060012, filed on Nov. 3, 2017.

(60) Provisional application No. 62/417,581, filed on Nov. 4, 2016.

(51) Int. Cl.
| | |
|---|---|
| *A01K 67/027* | (2006.01) |
| *C07K 16/28* | (2006.01) |
| *C12N 9/22* | (2006.01) |
| *C12N 15/11* | (2006.01) |
| *C12N 15/113* | (2010.01) |
| *C07K 16/00* | (2006.01) |

(52) U.S. Cl.
CPC .......... *A01K 67/0276* (2013.01); *C07K 16/00* (2013.01); *C07K 16/2818* (2013.01); *C12N 9/22* (2013.01); *C12N 15/11* (2013.01); *C12N 15/113* (2013.01); *A01K 2217/075* (2013.01); *A01K 2227/105* (2013.01); *A01K 2227/107* (2013.01); *A01K 2267/01* (2013.01); *C07K 2317/10* (2013.01); *C07K 2317/51* (2013.01); *C07K 2317/522* (2013.01); *C07K 2317/92* (2013.01); *C12N 2310/20* (2017.05); *C12N 2800/80* (2013.01)

(58) Field of Classification Search
CPC ............ A01K 67/0276; A01K 2267/01; C07K 16/00; C07K 2317/51; C07K 2317/522
USPC ...................................................... 800/18, 3
See application file for complete search history.

(56) References Cited

U.S. PATENT DOCUMENTS

| | | | |
|---|---|---|---|
| 4,816,567 A | 3/1989 | Cabilly | |
| 5,731,168 A | 3/1998 | Carter | |
| 5,821,337 A | 10/1998 | Carter | |
| 6,824,978 B1 | 11/2004 | Cox, III | |
| 6,982,321 B2 | 1/2006 | Winter | |
| 7,087,409 B2 | 8/2006 | Barbas, III | |
| 7,527,791 B2 | 5/2009 | Adams | |
| 8,546,553 B2 | 10/2013 | Terns | |
| 8,697,359 B1 | 4/2014 | Zhang | |
| 8,754,287 B2 | 6/2014 | Macdonald | |
| 8,883,150 B2 | 11/2014 | Craig | |
| 10,660,316 B2 | 5/2020 | Cui et al. | |
| 2010/0076057 A1 | 3/2010 | Sontheimer | |
| 2010/0093617 A1 | 4/2010 | Barrangou | |
| 2010/0122358 A1 | 5/2010 | Brueggemann | |
| 2011/0217739 A1 | 9/2011 | Terns | |
| 2012/0151610 A1 | 6/2012 | Craig | |
| 2013/0011828 A1 | 1/2013 | Barrangou | |
| 2013/0326645 A1 | 12/2013 | Cost | |
| 2013/0330778 A1 | 12/2013 | Zeiner | |
| 2014/0068797 A1 | 3/2014 | Doudna | |
| 2014/0073015 A1 | 3/2014 | Zhao | |
| 2014/0090113 A1 | 3/2014 | Cogan | |
| 2014/0093941 A1 | 4/2014 | Terns | |
| 2014/0199767 A1 | 7/2014 | Barrangou | |
| 2019/0261611 A1 | 8/2019 | Cui | |

FOREIGN PATENT DOCUMENTS

| | | |
|---|---|---|
| CN | 103388006 B | 10/2015 |
| CN | 103725710 B | 10/2015 |
| WO | WO199418313 A1 | 8/1994 |
| WO | WO199509233 A1 | 4/1995 |
| WO | WO199627011 A1 | 9/1996 |
| WO | WO2006081430 A2 | 8/2006 |
| WO | WO2006081430 A3 | 8/2006 |
| WO | WO2007025097 A2 | 3/2007 |

(Continued)

OTHER PUBLICATIONS

A1360-Product Description (2019). "5-Amino-2,3-dicyano-1,4-naphthoquinone", 2 pages.
Abbas et al. (2000). Cellular and Mol. Immunology, 4th ed. (W.B. Saunders, Co.), 6 pages.
Accession No. AY386696 (Aug. 23, 2003). "Oryctolagus Cuniculus Clone 27N5," Complete Sequence, 31 pages.
AF1086-Product Description (Feb. 6, 2018). "Human PD-1 Antibody," 9 pages.
Almagro, J. et al. (Jan. 2008). "Humanization of Antibodies," Frontiers in Bioscience 13:1619-1633.

(Continued)

*Primary Examiner* — Valarie E Bertoglio
(74) *Attorney, Agent, or Firm* — MORRISON & FOERSTER LLP

(57) ABSTRACT

The present application provides genetically modified non-human animals and methods for producing heavy chain-only antibodies (HcAbs), wherein the genetically modified non-human animal comprises a germline genome comprising an engineered immunoglobulin heavy chain (IgH) allele at an endogenous IgH locus, wherein the engineered IgH allele lacks functional gene segments encoding CH1 domains of all endogenous IgG subclasses. In some embodiments, a genetically modified mouse is provided, comprising an engineered IgH allele that lacks a functional endogenous gene segment encoding Cγ3, Cγ1, Cγ2b and CH1 exon of Cγ2c. Further provided are HcAbs or derivatives thereof produced by the genetically modified non-human animals.

11 Claims, 6 Drawing Sheets

Specification includes a Sequence Listing.

(56) References Cited

FOREIGN PATENT DOCUMENTS

| | | |
|---|---|---|
| WO | WO2007025097 A3 | 3/2007 |
| WO | WO2010011961 A2 | 1/2010 |
| WO | WO2010011961 A3 | 1/2010 |
| WO | WO2010075424 A2 | 7/2010 |
| WO | WO2010075424 A3 | 7/2010 |
| WO | WO2011072204 A1 | 6/2011 |
| WO | WO2011072246 A2 | 6/2011 |
| WO | WO2011072246 A3 | 6/2011 |
| WO | WO2013061098 A2 | 5/2013 |
| WO | WO2013061098 A3 | 5/2013 |
| WO | WO2013141680 A1 | 9/2013 |
| WO | WO2013142578 A1 | 9/2013 |
| WO | WO2013144567 A1 | 10/2013 |
| WO | WO2013163628 A2 | 10/2013 |
| WO | WO2013163628 A3 | 10/2013 |
| WO | WO2013169802 A1 | 11/2013 |
| WO | WO2013176772 A1 | 11/2013 |
| WO | WO2013181440 A1 | 12/2013 |
| WO | WO2013188037 A2 | 12/2013 |
| WO | WO2013188037 A3 | 12/2013 |
| WO | WO2013188522 A2 | 12/2013 |
| WO | WO2013188522 A3 | 12/2013 |
| WO | WO2013188638 A2 | 12/2013 |
| WO | WO2013188638 A3 | 12/2013 |
| WO | WO2013192278 A1 | 12/2013 |
| WO | WO2014018423 A2 | 1/2014 |
| WO | WO2014018423 A3 | 1/2014 |
| WO | WO2014018423 A8 | 1/2014 |
| WO | WO2014022702 A2 | 2/2014 |
| WO | WO2014022702 A3 | 2/2014 |
| WO | WO2014039872 A1 | 3/2014 |
| WO | WO2014065596 A1 | 5/2014 |
| WO | 2014130690 A1 | 8/2014 |

OTHER PUBLICATIONS

Baca, M. et al. (Apr. 18, 1997). "Antibody Humanization Using Monovalent Phage Display," J. Biol. Chem. 272 (16):10678-10684.

Brandt, C.R. et al. (Jul. 1984). "Loss of a Consensus Splice Signal in a Mutant Immunoglobulin Gene Eliminates the CH1 Domain Exon from the mRNA," Molecular and Cellular Biology. 4(7):1270-1277.

Brennan, M. et al. (Jul. 5, 1985). "Preparation of Bispecific Antibodies by Chemical Recombination of Monoclonal Immunoglobulin G1 Fragments," Science 229:81-83.

Brodeur, B.R. et al. (1987). "Mouse-Human Myeloma Partners for the Production of Heterohybridomas," in Monoclonal Antibody Production Techniques and Applications, pp. 51-63.

Carter, P. et al. (May 1992). "Humanization of an Anti-p185HER2 Antibody For Human Cancer Therapy," Proc. Natl. Acad. Sci. USA 89:4285-4289.

Choo, Y. et al. (Nov. 1994). "Toward A Code For The Interactions Of Zinc Fingers With DNA: Selection Of Randomized Fingers Displayed On Phage," Proc. Natl. Acad. Sci. USA 91(23):11163-11167.

Choo, Y. et al. (Oct. 13, 2005). "SPdb—A Signal Peptide Database," BMC Bioinformatics 6:249, 8 pages.

Cunningham, B.C. et al. (Jun. 2, 1989). "High-Resolution Epitope Mapping of hGH-Receptor Interactions by Alanine-Scanning Mutagenesis," Science 244:1081-1085.

Dall'Acqua, W.F. et al. (2005). "Antibody Humanization by Framework Shuffling," Methods 36:43-60.

Drabek, D. et al. (Dec. 19, 2016). "Expression Cloning and Production of Human Heavy-Chain-Only Antibodies From Murine Transgenic Plasma Cells," Frontiers in Immunology, 7(619):1-10.

Goding, J.W. (1986). Monoclonal Antibodies: Principles and Practice, pp. 59-103.

International Preliminary Report on Patentability, dated May 7, 2019, filed Nov. 3, 2017, for PCT Application No. PCT/US2017/060012, 7 pages.

International Search Report and Written Opinion, dated Jun. 29, 2018, filed Nov. 3, 2017, for PCT Application No. PCT/US/00012, 12 pages.

Jamieson, A.C. et al. (May 1994). In Vitro Selection of Zinc Fingers With Altered DNA-Binding Specificity, Biochemistry 33(19):5689-5695.

Janssens, R. et al. (Oct. 10, 2006). "Generation Of Heavy-Chain-Only Antibodies In Mice," Proc. Natl. Acad. Sci. USA 103(41):15130-15135.

Kabat, E.A. et al. (1991). Sequences of Proteins of Immunological Interest, Fifth Edition, National Institute of Health, Bethesda, Md., 10 pages.

Kashmiri, S.V.S. et al. (2005). "SDR Grafting—A New Approach to Antibody Humanization," Methods 36:25-34.

Klimka, A. et al. (2000). "Human Anti-CED30 Recombinant Antibodies By Guided Phage Antibody Selection Using Cell Panning," Br. J. Cancer 83(2):252-260.

Kostelny, S.A. et al. (Mar. 1, 1992), "Formation of a Bispecific Antibody by The Use of Leucine Zippers," J. Immunol. 148(5):1547-1553.

Kozbor, D. J. (Dec. 1984). "A Human Hybrid Myeloma For Production of Human Monoclonal Antibodies," Immunol. 133(6):3001-3005.

Köhler, G et al. (Aug. 7, 1975). "Continuous Culture of Fused Cells Secreting Antibody of Predefined Specificity," Nature, 256:495-497.

Morimoto, K. et al. (1992). "Single-Step Purification of F(AB')2 Fragments of Mouse Monoclonal Antibodies (Immunoglobulins G1) By Hydrophobic Interaction High Performance Liquid Chromatography Using TSKgel Phenyl-5PW," J. Biochem. Biophys. Method 24:107-117.

Morrison, S.L. et al. (Nov. 1984). "Chimeric Human Antibody Molecules: Mouse Antigen-Binding Domains With Human Constant Region Domains," Proc. Natl. Acad. Sci. USA 81:6851-6855.

Munson, P.J. et al. (1980). "Ligand: A Versatile Computerized Approach for Characterization of Ligand-Binding Systems," Anal. Biochem. 107:220-239.

Nguyen, V.K. et al. (1999). "Loss Of Splice Consensus Signal Is Responsible For The Removal Of The Entire CH1 Domain Of The Functional Camel IGG2A Heavy-Chain Antibodies," Molecular Immunology 36(8):515-524.

Osbourn, J. et al. (2005). "From Rodent Regents to Human Therapeutics Using Antibody Guided Selection," Methods 36:61-68.

Padlan, E.D. (1991). "A Possible Procedure for Reducing the Immunogenicity of Antibody Variable Domains While Preserving Their Ligand-Binding Properties," Mol. Immunol. 28(4/5):489-498.

Plückthun, A. (1992). "Mono- and Bivalent Antibody Fragments Producted in Escherichia coli: Engineering, Folding and Antigen Binding," Immunol. Revs. 130:151-188.

Presta, L.G. et al. (Sep. 1, 1993). "Humanization of an Antibody Directed Against IgE," J. Immunol. 151 (2):2623-2632.

Queen, C. et al. (Dec. 1989). "A Humanized Antibody That Binds to the Interleukin 2 Receptor," Proc. Natl Acad. Sci. USA 86:10029-10033.

Rebar, E.J. et al. (Feb. 4, 1994). "Zinc Finger Phage: Affinity Selection of Fingers With New DNA-Binding Specificities," Science 263:671-673.

Riechmann, L. et al. (Mar. 1988). "Reshaping Human Antibodies for Therapy," Nature 332:323-329.

Rosok, M.J. et al. (Sep. 13, 1996). "A Combinatorial Library Strategy for the Rapid Humanization of Anticarcinoma BR96 Fab," J. Biol. Chem. 271(37):22611-22618.

Sander et al. (Apr. 2014). "CRISPR-Cas Systems for Genome Editing, Regulation and Targeting," Nature Biotechnology 32(4):347-355, 24 pages.

Sims, M.J. et al. (Aug. 15, 1993). "A Humanized CD18 Antibody Can Block Function Withoud Cell Destruction," J. Immunol. 151:2296-2308.

Skerra, A. (1993). "Bacterial Expression of Immunoglobulin Fragments," Curr. Opinion in Immunol. 5:256-262.

(56) References Cited

OTHER PUBLICATIONS

Tutt, A. et al. (Jul. 1, 1991), "Trispecific F(ab')3 Derivatives That Use Cooperative Signaling Via The TCR/CD3 Complex and CD2 to Activate and Redirect Resting Cytotoxic T Cells," J. Immunol. 147:60-69.

Zou, X. et al. (2005). "Expression of a Dromedary Heavy Chain-Only Antibody and B Cell Development in the Mouse," Journal of Immunology, 175:3769-3779.

Zou, X. et al. (Dec. 24, 2007, e-pub. Dec. 17, 2007). "Heavy Chain—Only Antibodies Are Spontaneously Produced In Light Chain—Deficient Mice," The Journal of Experimental Medicine 204(13):3271-3283.

Final Office Action, dated Dec. 13, 2019, for U.S. Appl. No. 16/401,029, filed May 1, 2019, 7 pages.

Non-Final Office Action, dated Sep. 3, 2019, for U.S. Appl. No. 16/401,029, filed May 1, 2019, 25 pages.

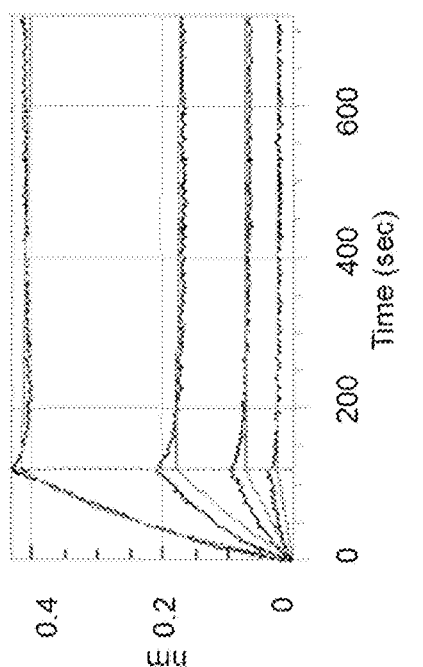
FIG. 6A  KD = 1.33 nM
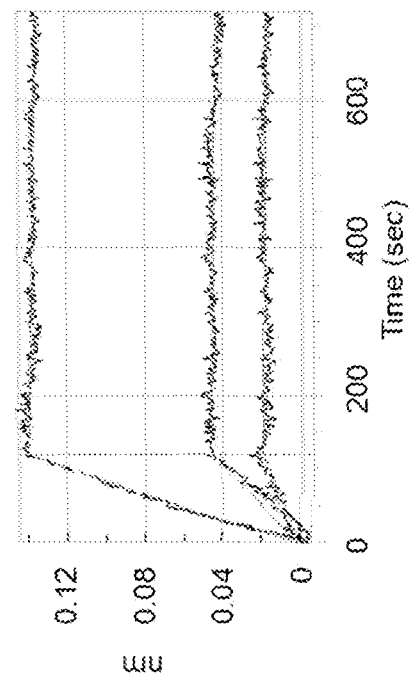
FIG. 6C  KD < 1 pM
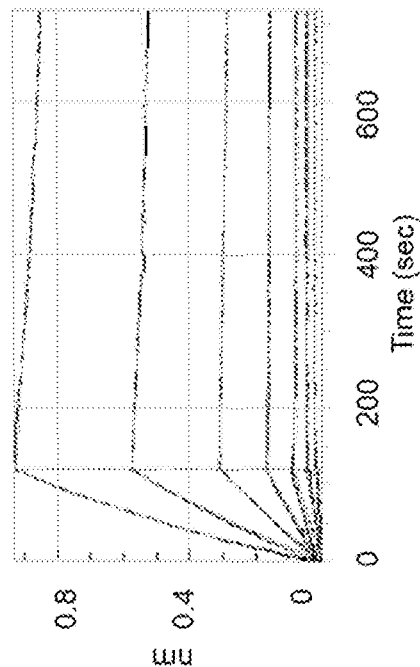
FIG. 6B  KD = 50.1 pM
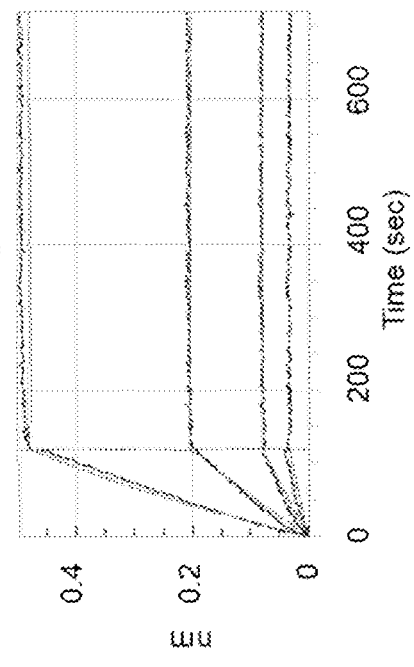
FIG. 6D  KD = 2.63 nM

GENETICALLY MODIFIED NON-HUMAN ANIMALS AND METHODS FOR PRODUCING HEAVY CHAIN-ONLY ANTIBODIES

CROSS REFERENCE TO RELATED APPLICATIONS

This divisional application of U.S. application Ser. No. 16/401,029, filed on May 1, 2019, which is a continuation application of International Application No. PCT/US2017/060012, filed on Nov. 3, 2017, which claims priority benefit of U.S. Provisional Application No. 62/417,581, filed Nov. 4, 2016, the contents of which are incorporated herein by reference in their entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 786192000110SEQLIST.txt, date recorded: Apr. 10, 2020, size: 11 KB).

FIELD OF THE INVENTION

The present invention relates to genetically modified non-human animals and methods for producing heavy chain-only antibodies.

BACKGROUND OF THE INVENTION

Conventional antibodies of vertebrates are composed of paired heavy (H) and light (L) polypeptide chains. Absence of heavy chain (HC) or light chain (LC) expression leads to arrest of B cell development. Some species such as camelids (camels, dromedaries and llamas), sharks, and ratfish produce HC-only antibodies (HcAb) that lack L-chains as part of their normal B cell development and repertoire. The antigen-binding site, a single-variable domain (VHH), resembles VH of conventional Abs. In Camelidae, these heavy-chain antibodies (HcAbs) belong to IgG2 and IgG3 isotypes, and their variable domains are subject to somatic hypermutation. Thus, the camelid HcAbs are affinity-matured and functional in antigen binding.

Transgenic mice containing rearranged dromedary γ2a heavy chains have been generated. The dromedary transgene is expressed as heavy chain-only antibodies. See, Zou X. et al, *Journal of Immunology,* 175: 3769-3779 (2005). Mice containing various non-rearranged chimeric HcAb loci have also been generated. See, Janssens R. et al. *PNAS,* 103 (41): 15130-15135 (2006). The limited number of VH fragments in the transgenic HcAb loci, however, results in some antigens not being recognized by these mice, despite potent antigen response by wildtype mice. See, Janssens R. et al. *PNAS,* 103 (41): 15130-15135 (2006); Drabe D. et al. *Frontiers in Immunology,* 7 (619): 1-10 (2016); and U.S. Pat. No. 8,883,150. Heavy chain-only antibodies are also spontaneously produced in light chain deficient mice, but in these mice, B cell development is blocked at the immature B cell stage. See, Zou X. et al. *JEM,* 204(13): 3271-3283 (2007).

The disclosures of all publications, patents, patent applications and published patent applications referred to herein are hereby incorporated herein by reference in their entirety.

BRIEF SUMMARY OF THE INVENTION

The present application provides genetically modified non-human animals, methods, and kits for producing heavy chain-only antibodies (HcAbs). Also provided are HcAbs and derivatives thereof produced by the genetically modified non-human animals and/or using the methods described herein.

One aspect of the present application provides a genetically modified non-human animal comprising a germline genome comprising an engineered immunoglobulin heavy chain (IgH) allele at an endogenous IgH locus, wherein the engineered IgH allele lacks functional endogenous gene segments encoding CH1 domains of all endogenous IgG subclasses. In some embodiments, the engineered. IgH allele comprises a defective splice site immediately after the CH1 exon of an endogenous Cγ gene. In some embodiments, the engineered IgH allele lacks the CH1 exon of an endogenous Cγ gene. In some embodiments, the engineered IgH allele lacks an endogenous Cγ gene.

In some embodiments according to any one of the genetically modified non-human animals as described above, the genetically modified non-human animal does not express IgG molecules comprising light chains. In some embodiments, the engineered IgH allele does not comprise rearranged genes. In some embodiments, the genetically modified non-human animal is homozygous for the engineered IgH allele. In some embodiments, the engineered IgH allele does not contain human V, D, or J genes. In some embodiments, the engineered IgH allele does not contain camelid V, D, or J genes. In some embodiments, the engineered IgH allele does not comprise an exogenous sequence. In some embodiments, the genetically modified non-human animal has a fully functional endogenous light chain locus. In some embodiments, the engineered IgH allele comprises a fully functional Cμ gene. In some embodiments, the genetically modified non-human animal expresses wildtype IgM, IgD, IgA, and IgE proteins.

In some embodiments, the genetically modified non-human animal is a rodent. In some embodiments, the rodent is a mouse. In some embodiments, the engineered IgH allele lacks an endogenous gene segment comprising Cγ3, Cγ1, Cγ2b and CH1 exon of Cγ2c. In some embodiments, the endogenous gene segment is about 72.7 kb long. In some embodiments, the engineered IgH allele comprises a nucleotide sequence of no more than about 250 nucleotides (such as no more than about 200, or 100 nucleotides) long, and wherein the nucleotide sequence comprises SEQ ID NO: 27 and SEQ ID NO: 28. In some embodiments, the engineered. IgH allele comprises a nucleotide sequence selected from SEQ ID NOs: 1-25.

In some embodiments, the rodent is a rat. In some embodiments, the engineered IgH allele lacks an endogenous gene segment comprising Cγ2c, Cγ2a, Cγ1 and CH1 exon of Cγ2b. In some embodiments, the endogenous gene segment is about 140 kb long.

In some embodiments, the genetically modified non-human animal is a rabbit. In some embodiments, the engineered IgH allele lacks a functional endogenous CH1 exon of Cγ. In some embodiments, the engineered IgH allele lacks the endogenous CH1 exon of Cγ.

One aspect of the present application provides a method of producing a genetically modified non-human animal capable of producing heavy chain-only antibodies (HcAb), comprising introducing one or more loss-of-function mutations to gene segments encoding the CH1 domains of all endogenous IgG subclasses at an endogenous immunoglobulin heavy chain (IgH) locus in the germline genome of a non-human animal, thereby providing the genetically modified non-human animal. In some embodiments, the one or more mutations comprise a loss-of-function mutation to the splice site immediately after the CH1 exon of a Cγ gene. In some embodiments, the one or more mutations comprise deletion of a Cγ gene or the CH1 exon of a Cγ gene. In some embodiments, the non-human animal is a mouse, and wherein the method comprises deleting an endogenous gene segment comprising Cγ3, Cγ1, Cγ2b and CH1 exon of Cγ2c from the endogenous IgH locus. In some embodiments, the non-human animal is a rat, and wherein the method comprises deleting an endogenous gene segment comprising Cγ2c, Cγ2a, Cγ1 and CH1 exon of Cγ2b from the endogenous IgH locus. In some embodiments, the non-human animal is a rabbit, and wherein the method comprises deleting the endogenous CH1 exon of Cγ from the endogenous IgH locus.

In some embodiments according to any one of the methods of producing a genetically modified non-human animal as described above, the method comprises introducing the one or more mutations to the endogenous IgH locus in a one-cell embryo of a non-human animal, implanting the embryo in a surrogate animal, and breading the surrogate animal to produce the genetically modified non-human animal. In some embodiments, the one or more mutations are introduced to the endogenous IgH locus by CRISPR/Cas9 genome editing. In some embodiments, the method comprises injecting an mRNA encoding Cas 9, a first sgRNA targeting the first intron (or 5'UTR) upstream of the CH1 exon of the first Cγ gene in the endogenous IgH locus, and a second sgRNA targeting the first intron downstream of the CH1 exon of the last Cγ gene in the endogenous IgH locus into a one-cell embryo of a non-human animal, implanting the embryo into a surrogate animal, and breeding the surrogate animal to produce the genetically modified non-human animal.

In some embodiments, there is provided a genetically modified non-human animal produced by any one of the methods of producing a genetically modified non-human animal as described above.

In some embodiments according to any one of the genetically modified non-human animals described above, the genetically modified non-human animal is fertile. In some embodiments, the genetically modified non-human animal has substantially normal B Cell development and maturation. In some embodiments, the genetically modified non-human animal expresses a plurality of IgG proteins in response to an antigen, wherein the plurality of IgG proteins do not contain light chains. In some embodiments, the genetically modified non-human animal has substantially normal V-D-J recombination, substantially normal classic switch recombination (CSR), and substantially normal somatic hypermutations.

Another aspect of the present application provides a method of producing a heavy chain-only antibody (HcAb) that specifically binds to an antigen of interest, comprising: (a) immunizing any one of the genetically modified non-human animals described above with the antigen; and (b) obtaining a HcAb that specifically binds to the antigen from the immunized genetically modified non-human animal, thereby producing the HcAb. In some embodiments, step (h) comprises: (i) obtaining a cell comprising a nucleic acid encoding the heavy chain of the HcAb; (ii) obtaining the nucleic acid from the cell; and (iii) expressing the nucleic acid in a host cell to provide the HcAb. In some embodiments, the method further comprises producing a chimeric HcAb based on the CDR sequences of the HcAb. In some embodiments, the method further comprises affinity maturation of the HcAb.

One aspect of the present application provides a heavy chain-only antibody (HcAb) produced by any one of the methods of producing a HcAb as described above, and a heavy chain-only antibody (HcAb) isolated from any one of the genetically modified non-human animals described above. In some embodiments, the HcAb is monoclonal. In some embodiments, the HcAb is polyclonal. In some embodiments, there is provided a fusion protein comprising any one of the HcAbs described above, or an antigen-binding fragment thereof.

Also provided is a B cell isolated from any one of the genetically modified non-human animals described above, and a hybridoma produced based on the B cell.

These and other aspects and advantages of the present invention will become apparent from the subsequent detailed description and the appended claims. It is to be understood that one, some, or all of the properties of the various embodiments described herein may be combined to form other embodiments of the present invention.

BRIEF DESCRIPTION OF THE DRAWINGS

FIGS. 6A-6D show kinetic analysis of PD-1 binding of heavy chain-only antibodies produced by genetically modified mice that were immunized against human PD-1.

DETAILED DESCRIPTION OF THE INVENTION

Figure 1:
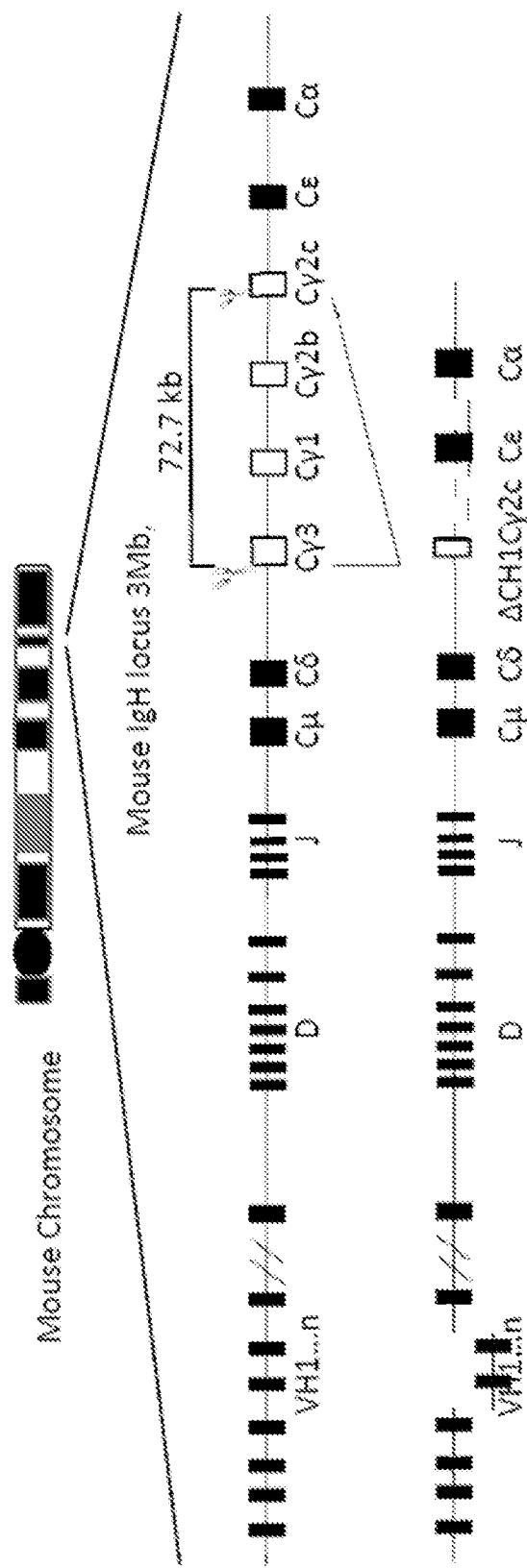
FIG. 1 illustrates mouse chromosome 12 and mouse IgH locus at 12qF1 (top), wild-type IgH locus, and a genetically modified IgH locus with a 72.7 kb deletion of gene fragments encoding IgG3, IgG1, IgG2b, and CH1 of IgG2c.

The present application provides genetically modified non-human animals, methods, and kits for producing heavy chain-only antibodies (HcAbs) and applications thereof. In some embodiments, the genetically modified non-human animal lacks functional gene segments encoding the CH1 domains of all endogenous IgG subclasses. In some embodiments, a genetically modified mouse is provided, wherein each of its endogenous immunoglobulin heavy chain (IgH) loci lacks an endogenous gene segment comprising Cγ2c, Cγ2a, Cγ1 and CH1 exon of Cγ2b. In some embodiments, a genetically modified rat is provided, wherein each of its endogenous IgH loci lacks an endogenous gene segment comprising Cγ2c, Cγ2a, Cγ1 and CH1 exon of Cγ2b. In some embodiments, a genetically modified rabbit is provided, wherein each of its endogenous IgH loci lacks the endogenous CH1 exon of Cγ.

For example, using CRISPR/Cas9 zygote genome editing methods, inventors precisely knocked out from the endogenous IgH loci a large portion (about 72.7 kb) of the mouse genome, which encompasses gene segments encoding the constant regions of all IgGs except for the CH2 and CH3 regions of IgG2c. The entire mouse immunoglobulin variable region and the constant regions of IgM, IgD, IgA, and IgE, however, were left intact. Surprisingly, the immunogenetically modified mice were viable and fertile, with an immune system resembling that of wildtype mice. Their B cells underwent substantially normal development and maturation processes. In response to antigenic challenges, the mice produced functional heavy chain-only antibodies, which were naturally matured and had high affinity to the antigens.

Camelidae are produce naturally matured functional HcAbs, and in addition, they produce classical antibodies that comprise heavy and light chains. Prior to this study, transgenic and chimeric non-human animals have been made to produce HcAbs, but they produced a mixture of HcAbs and conventional IgGs having both heavy chains and light chains. In contrast, the genetically modified non-human animals described herein are capable of using the full endogenous heavy chain variable repertoire to produce IgG molecules that are exclusively heavy chain-only antibodies. The genetically modified non-human animals described herein provide a robust and versatile platform for the discovery and engineering of therapeutic antibodies with enhanced antigen binding repertoire diversification and novel antigen-receptor properties.

Accordingly, one aspect of the present application provides a genetically modified non-human animal comprising a germline genome comprising an engineered immunoglobulin heavy chain (IgH) allele at an endogenous IgH locus, wherein the engineered IgH allele lacks functional endogenous gene segments encoding CH1 domains of all endogenous IgG subclasses.

In some embodiments, there is provided a genetically modified mouse comprising a germline genome comprising an engineered IgH allele at an endogenous IgH locus, wherein the engineered IgH allele lacks an endogenous gene segment comprising Cγ3, Cγ1, Cγ2b and CH1 exon of Cγ2c.

Also provided are methods of producing a genetically modified non-human animal capable of producing HcAbs, genetically modified non-human embryos, cells, and constructs for making the genetically modified embryos, cells and animals. Further provided are methods of producing HcAbs, HcAbs produced by the genetically modified non-human animals and derivatives thereof, and kits and articles manufacture useful for the methods described herein.

I. Definitions

Unless otherwise defined, scientific and technical terms used in connection with the present invention shall have the meanings that are commonly understood by those of ordinary skill in the art. Further, unless otherwise required by context or expressly indicated, singular terms shall include pluralities and plural terms shall include the singular.

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

The terms "heavy chain-only antibody" and "HcAb" are used interchangeably herein to refer to a functional antibody, which comprises heavy chains, but lacks the light chains usually found in classical antibodies. Camelid animals (such as camels, llamas, or alpacas) are known to produce HcAbs.

As used herein, "classical" or "conventional" antibody refers to an antibody having both heavy (H) chains and light (L) chains. Classical full-length antibodies are usually heterotetrameric glycoproteins of about 150,000 Daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light chain variable domain is aligned with the variable domain of the heavy chain. Particular amino acid residues are believed to form an interface between the light chain and heavy chain variable domains.

The terms "constant domain" and "constant regions" are used herein interchangeably to refer to the portion of an immunoglobulin molecule having a more conserved amino acid sequence relative to the other portion of the immunoglobulin, the variable domain, which contains the antigen binding site. The constant domains of classical full-length antibodies contain the $C_H1$, $C_H2$ and $C_H3$ domains (collectively, CH) of the heavy chain and the CHL (or CL) domain of the light chain.

The "variable region" or "variable domain" of an antibody refers to the amino-terminal domains of the heavy or light chain of the antibody. The variable domain of the heavy chain may be referred to as "VH," The variable domain of the heavy chain in heavy chain-only antibodies may be referred to as "VHH," The variable domain of the light chain may be referred to as "VL." These domains are generally the most variable parts of an antibody and contain the antigen-binding sites.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called hypervariable regions (HVRs) both in the light-chain and the heavy-chain variable domains, Generally, native four-chain antibodies comprise six HVRs; three in the $V_H$ (H1, H2, H3), and three in the $V_L$ (L1, L2, L3). Heavy chain-only antibodies comprise three HVRs in the $V_H$ (H1, H2, H3). HVRs generally comprise amino acid residues front the hypervariable loops and/or from the "complementarity determining regions" (CDRs). CDRs being of highest sequence variability and/or involved in antigen recognition. The more highly conserved portions of variable domains are called the framework regions (FR). The variable domains of native heavy and light chains each comprise four FR regions, largely adopting a beta-sheet configuration, connected by three HVRs, which form loops connecting, and in some cases forming part of, the beta-sheet structure. The HVRs in each chain are held together in close proximity by the FR regions and, with the HVRs from the other chain, contribute to the formation of the antigen-binding site of antibodies (see Kabat et al., Sequences of Proteins of Immunological Interest. Fifth Edition, National Institute of Health, Bethesda, Md. (1991)). The constant domains are not involved directly in the binding of an antibody to an antigen, but exhibit various effector functions, such as participation of the antibody in antibody-dependent cellular toxicity.

The term "heavy chain" as used herein refers to a polypeptide comprising at least a heavy chain variable region, with or without a leader sequence. In some embodiments, a heavy chain comprises at least a portion of a heavy chain constant region. The term "full-length heavy chain" as used herein refers to a polypeptide comprising a heavy chain variable region and a heavy chain constant region, with or without a leader sequence.

The term "heavy chain variable region" as used herein refers to a region comprising heavy chain HVR1, framework (FR) 2, HVR2, FR3, and HVR3. For example, a heavy chain variable region may comprise heavy chain CDR1, framework (FR) 2, CDR2, FR3, and CDR3. In some embodiments, a heavy chain variable region also comprises at least a portion of an FR1 and/or at least a portion of an FR4.

The term IgG "isotype" or "subclass" as used herein is meant any of the subclasses of immunoglobulins defined by the chemical and antigenic characteristics of their constant regions. Exemplary IgG subclasses include, but are not limited to IgG1, IgG2a, IgG2b, IgG2c, and IgG3. In many animals, IgG is encoded by the Cγ gene in the immunoglobulin heavy chain locus. The immunoglobulin heavy chain locus is also referred herein as the "IgH locus." Different IgG subclasses are encoded by different Cγ genes, including, for example, Cγ1 for IgG1, Cγ2a for IgG2a, Cγ2b for IgG2b, Cγ2c for IgG2c, and Cγ3 for IgG3.

Depending on the amino acid sequences of the constant domains of their heavy chains, antibodies (immunoglobulins) can be assigned to different classes, There are five major classes of immunoglobulins: IgA, IgD, IgE, IgG, and IgM, and several of these may be further divided into subclasses (isotypes), e.g., IgG-1, IgG2, IgG3, IgG4, IgA1, and IgA2. The heavy chain constant domains that correspond to the different classes of immunoglobulins are called α, γ, ε, γ, and μ, respectively. The subunit structures and three-dimensional configurations of different classes of immunoglobulins are well known and described generally in, for example, Abbas et al. Cellular and Mol. Immunology, 4th ed. (W. B. Saunders, Co., 2000). An antibody may be part of a larger fusion molecule, formed by covalent or non-covalent association of the antibody with one or more other proteins or peptides.

The term "light chain" as used herein refers to a polypeptide comprising at least a light chain variable region, with or without a leader sequence. In some embodiments, a light chain comprises at least a portion of a light chain constant region. The term "full-length light chain" as used herein refers to a polypeptide comprising a light chain variable region and a light chain constant region, with or without a leader sequence.

The term "light chain variable region" as used herein refers to a region comprising light chain HVR1, framework (FR) 2, HVR2, FR3, and HVR3. In some examples the light chain variable region comprises light chain CDR1, framework (FR) 2, CDR2, FR3, and CDR3. In some embodiments, a light chain variable region also comprises an FR1 and/or an FR4.

The term "light chain constant region" as used herein refers to a region comprising a light chain constant domain, $C_L$. Nonlimiting exemplary light chain constant regions include λ and κ.

The terms "full length antibody," "intact antibody" and "whole antibody" are used herein interchangeably to refer to an antibody in its substantially intact form, not antibody fragments as defined below. The terms particularly refer to an antibody with heavy chains that contain an Fc region.

"Antibody fragments" comprise a portion of an intact antibody, preferably comprising the antigen binding region thereof. In some embodiments, the antibody fragment described herein is an antigen-binding fragment, Examples of antibody fragments include VH domain single-chain antibody molecules; and multispecific antibodies formed from antibody fragments.

The term "monoclonal antibody" as used herein refers to an antibody obtained from a population of substantially homogeneous antibodies, e.g., the individual antibodies comprising the population are identical except for possible mutations, e.g., naturally occurring mutations, that may be present in minor amounts. Thus, the modifier "monoclonal" indicates the character of the antibody as not being a mixture of discrete antibodies. In certain embodiments, such a monoclonal antibody typically includes an antibody comprising a polypeptide sequence that binds a target, wherein the target-binding polypeptide sequence was obtained by a process that includes the selection of a single target binding polypeptide sequence from a plurality of polypeptide sequences. For example, the selection process can be the selection of a unique clone from a plurality of clones, such as a pool of hybridoma clones, phage clones, or recombinant DNA clones. It should be understood that a selected target binding sequence can be further altered, for example, to improve affinity for the target, to humanize the target binding sequence, to improve its production in cell culture, to reduce its immunogenicity in vivo, to create a multispecific antibody, etc., and that an antibody comprising the altered target binding sequence is also a monoclonal antibody of this invention. In contrast to polyclonal antibody preparations, which typically include different antibodies directed against different determinants (epitopes), each monoclonal antibody of a monoclonal antibody preparation is directed against a single determinant on an antigen. In addition to their specificity, monoclonal antibody preparations are advantageous in that they are typically uncontaminated by other immunoglobulins.

A "chimeric antibody" as used herein refers to an antibody in which a portion of the heavy is derived from a particular source or species, while the remainder of the heavy chain is derived from a different source or species. In some embodiments, a chimeric antibody refers to an antibody comprising at least one variable region from a first species (such as mouse, rat, cynomolgus monkey, etc.) and at least one constant region from a second species (such as human, cynomolgus monkey, etc.). In some embodiments, a chimeric antibody comprises at least one mouse variable region and at least one human constant region. In some embodiments, a chimeric antibody comprises at least one rat variable region and at least one human constant region. In some embodiments, a chimeric antibody comprises at least one rabbit variable region and at least one human constant region. In some embodiments, all of the variable regions of a chimeric antibody are from a first species and all of the constant regions of the chimeric antibody are from a second species.

A "humanized antibody" as used herein refers to an antibody in which at least one amino acid in a framework region of a non-human variable region has been replaced with the corresponding amino acid from a human variable region. In some embodiments, a humanized antibody comprises at least one human constant region or fragment thereof.

An "HVR-grafted antibody" as used herein refers to a humanized antibody in which one or more hypervariable regions (HVRs) of a first (non-human) species have been grafted onto the framework regions (FRs) of a second (human) species. In some examples, a "CDR-grafted antibody" as used herein refers to a humanized antibody in which one or more complementarity determining regions (CDRs) of a first (non-human) species have been grafted onto the framework regions (FRs) of a second (human) species.

An "acceptor human framework" for the purposes herein is a framework comprising the amino acid sequence of a light chain variable domain ($V_L$) framework or a heavy chain variable domain ($V_H$) framework derived from a human immunoglobulin framework or a human consensus framework, as defined below. An acceptor human framework derived from a human immunoglobulin framework or a human consensus framework may comprise the same amino acid sequence thereof, or it may contain amino acid sequence changes. In some embodiments, the number of amino acid changes are 10 or less, 9 or less, 8 or less, 7 or less, 6 or less, 5 or less, 4 or less, 3 or less, or 2 or less.

"Affinity" refers to the strength of the sum total of noncovalent interactions between a single binding site of a molecule (e.g., an antibody) and its binding partner (e.g., an antigen). The affinity of a molecule X for its partner Y can generally be represented by the dissociation constant ($K_d$). Affinity can be measured by common methods known in the art, including those described herein.

An "affinity matured" antibody refers to an antibody with one or more alterations in one or more hypervariable regions (HVRs) compared to a parent antibody which does not possess such alterations, such alterations resulting in an improvement in the affinity of the antibody for antigen. In some examples, an affinity matured antibody refers to an antibody with one or more alterations in one or more complementarity determining regions (CDRs) compared to a parent antibody which does not possess such alterations, such alterations resulting in an improvement in the affinity of the antibody for antigen.

The term "substantially similar" or "substantially the same" as used herein, denotes a sufficiently high degree of similarity between two or more numeric values such that one of skill in the art would consider the difference between the two or more values to be of little or no biological and/or statistical significance within the context of the biological characteristic measured by said value. In some embodiments the two or more substantially similar values differ by no more than about any one of 5%, 10%, 15%, 20%, 25%, or 50%. "Substantially normal" as referred to a process in a subject means that the process in the subject (such as in a wildtype animal) is substantially similar to that in the control.

The term "leader sequence" refers to a sequence of amino acid residues located at the N-terminus of a polypeptide that facilitates secretion of a polypeptide from a mammalian cell. A leader sequence may be cleaved upon export of the polypeptide from the mammalian cell, forming a mature protein, Leader sequences may be natural or synthetic, and they may be heterologous or homologous to the protein to which they are attached.

The term "vector" is used to describe a polynucleotide that may be engineered to contain a cloned polynucleotide or polynucleotides that may be propagated in a host cell. A vector may include one or more of the following elements: an origin of replication, one or more regulatory sequences (such as, for example, promoters and/or enhancers) that regulate the expression of the polypeptide of interest, and/or one or more selectable marker genes (such as, for example, antibiotic resistance genes and genes that may be used in colorimetric assays, e.g., β-galactosidase). The term "expression vector" refers to a vector that is used to express a polypeptide of interest in a host cell.

A "host cell" refers to a cell that may be or has been a recipient of a vector or isolated polynucleotide, Host cells may be prokaryotic cells or eukaryotic cells. Exemplary eukaryotic cells include mammalian cells, such as primate or non-primate animal cells; fungal cells, such as yeast; plant cells; and insect cells. Nonlimiting exemplary mammalian cells include, but are not limited to, NSO cells, PER.C6® cells (Crucell), and 293 and CHO cells, and their derivatives, such as 293-6E and DG44 cells, respectively.

The term "isolated" as used herein refers to a molecule that has been separated from at least some of the components with which it is typically found in nature or produced. For example, a polypeptide is referred to as "isolated" when it is separated from at least some of the components of the cell in which it was produced. Where a polypeptide is secreted by a cell after expression, physically separating the supernatant containing the polypeptide from the cell that produced it is considered to be "isolating" the polypeptide. Similarly, a polynucleotide is referred to as "isolated" when it is not part of the larger polynucleotide (such as, for example, genomic DNA or mitochondrial DNA, in the case of a DNA polynucleotide) in which it is typically found in nature, or is separated from at least some of the components of the cell in which it was produced, e.g., in the case of an RNA polynucleotide. Thus, a DNA polynucleotide that is contained in a vector inside a host cell may be referred to as "isolated."

It is understood that embodiments of the invention described herein include "consisting" and/or "consisting essentially of" embodiments.

Reference to "about" a value or parameter herein includes (and describes) variations that are directed to that value or parameter per se. For example, description referring to "about X" includes description of "X".

As used herein, reference to "not" a value or parameter generally means and describes "other than" a value or parameter.

The term "about X-Y" used herein has the same meaning as "about X to about Y."

As used herein, the singular forms "a," "or," and "the" include plural referents unless the context clearly dictates otherwise.

II. Genetically Modified Non-Human Animals

The present application provides genetically modified non-human animals that produce heavy chain-only antibodies, i.e., antibodies that lack light chains. In some embodiments, the genetically modified non-human animal does not produce IgG molecules comprising light chains. In some embodiments, the genetically modified non-human animal does not produce any classical IgG molecules, i.e., antibodies that have both heavy chains and light chains.

In some embodiments, there is provided a genetically modified non-human animal comprising a germline genome comprising an engineered immunoglobulin heavy chain (IgH) allele at an endogenous IgH locus, wherein the engineered IgH allele lacks functional endogenous gene segments encoding CH1 domains of all endogenous IgG subclasses. In some embodiments, the genetically modified non-human animal is heterozygous for the engineered IgH allele. In some embodiments, the genetically modified non-human animal is homozygous for the engineered IgH allele. In some embodiments, the genetically modified non-human animal does not express IgG molecules comprising light chains. In some embodiments, the engineered IgH allele does not comprise rearranged genes. In some embodiments, the engineered IgH allele does not comprise exogenous sequences, such as human or camelid V, D, or J genes. In some embodiments, the genetically modified non-human animal has a fully functional endogenous light chain locus. In some embodiments, the engineered IgH allele comprises a fully functional Cμ gene. In some embodiments, the genetically modified non-human animal expresses wildtype IgM, IgA, IgD, and IgE proteins.

The germline genome of the genetically modified non-human animal may have more than one endogenous IgH loci. In some embodiments, the germline genome of the genetically modified non-human animal is diploid. In some embodiments, the genetically modified non-human animal is heterozygous for the engineered IgH allele, i.e., wherein only one of the two endogenous IgH loci comprises the engineered IgH allele. In some embodiments, the genetically modified non-human animal comprises a germline genome comprising a first engineered IgH allele at a first endogenous IgH locus, and a second different engineered IgH allele at the second endogenous IgH locus. In some embodiments, the genetically modified non-human animal is homozygous for the engineered IgH allele, i.e., wherein each of the two endogenous IgH loci comprises the engineered IgH allele.

In some embodiments, the engineered IgH allele comprises one or more mutations in the endogenous IgH locus, wherein the one or more mutations disable endogenous gene segments encoding the CH1 domains of all endogenous IgG subclasses. In some embodiments, the engineered IgH allele comprises one or more mutations selected from deletion of the CH1 exon of an endogenous Cγ gene, deletion of an endogenous Cγ gene, a mutation to the splice site immediately after the CH1 exon of an endogenous Cγ gene that leads to loss of the CH1 exon in mRNA transcripts of the Cγ gene, and combinations thereof. The one or more mutations can be a deletion, insertion, or substitution mutation of one or more nucleotide residues in the CH1 exon of an endogenous Cγ gene, the splice site immediately after the CH1 exon of an endogenous Cγ gene, or an endogenous Cγ gene.

In some embodiments, the engineered IgH allele lacks the CH1 exon of an endogenous Cγ gene. In some embodiments, the engineered IgH allele lacks the CH1 exon of each endogenous Cγ gene. In some embodiments, the engineered IgH allele lacks an endogenous Cγ gene. In some embodiments, wherein the endogenous IgH locus in a wildtype non-human animal comprises two or more endogenous Cγ genes, the one or more mutations comprise deletion of all Cγ genes except for the most downstream endogenous Cγ gene, and deletion of the CH1 exon of the most downstream endogenous Cγ gene at the endogenous IgH locus. "Downstream" or "upstream" as used herein in reference to a gene or cluster of genes at a locus is characterized by the orientation of transcription of the gene or cluster of genes at the locus. An upstream gene or gene segment yields a transcript 5' to the transcript of a downstream gene or gene segment.

In some embodiments, the engineered IgH allele comprises a defective splice site immediately after the CH1 exon of an endogenous Cγ gene. In some embodiments, each endogenous Cγ gene in the engineered IgH allele has a defective splice site immediately after the CH1 exon of the endogenous Cγ gene. In some embodiments, the defective splice site comprises a mutation, such as a point mutation, to the consensus sequence of the 5' splice site immediately after the CH1 exon of the endogenous Cγ gene. In some embodiments, the defective splice site has a point mutation to the first nucleotide ("+1" position) in the 5' splice site immediately after the CH1 exon of the endogenous Cγ gene, in some embodiments, the consensus sequence of the 5' splice site is GT. In some embodiments, the defective splice site comprises a G to A transversion mutation at the first nucleotide (i.e., G(+1) to A(+1) mutation) in the 5' splice site immediately after the CH1 exon of the endogenous Cγ gene. The defective splice site leads to loss of the CH1 exon in mRNA transcripts of the Cγ gene.

Camelidae, such camels, dromedaries and llamas, produce heavy-chain antibodies (HcAbs) of IgG2 and IgG3 isotypes. In the HcAb transcripts, the first domain of the constant region, CH1, is spliced out because of the loss of a consensus splice signal. The organization of the camel gamma constant heavy-chain genes obtained from a liver genomic library appears to be typical of all other mammalian gamma genes sequenced to date, with the tetrameric and homodimeric camelid IgGs originated from the same IgH locus. Each IgG-encoding gene contains the switch, CH1, hinge, CH2, CH3, M1 and M2 exons. Unlike the IgH loci in mice and human having heavy chain diseases, the camel gamma genes encoding HcAbs contain complete VDJ regions with no major structural defects, and the corresponding CH1 exons are intact. However, sequence analysis has revealed that the splicing site, immediately after the CH1 exon, is defective due to point mutations, especially the G(+1) to A(+1) transversion mutation seems to be detrimental. Such data suggests that the loss of the splice consensus signal is responsible for the removal of the entire CH1 domain in camel gamma heavy-chain only immunoglobulins. See, Nguyen V. K. et al. *Molecular immunology* 36 (1999) 515-524. Furthermore, HcAbs of the IgM class have not been found in camelids. Analyses of cDNA coding for the membrane forms of IgG and IgM present in camelids peripheral blood B cells are most consistent with the notion that the development of a B cell bearing homodimeric IgG passes through an IgM(+) stage, similar to the case for conventional IgGs.

Thus, in some embodiments, there is provided a genetically modified non-human animal comprising a germline genome comprising an engineered immunoglobulin heavy chain (IgH) allele at an endogenous IgH locus, wherein the engineered IgH allele comprises one or more mutations selected from deletion of the CH1 exon of an endogenous Cγ gene, deletion of an endogenous Cγ gene, a mutation to the splice site immediately after the CH1 exon of an endogenous Cγ gene that leads to loss of the CH1 exon in mRNA transcripts of the Cγ gene, and combinations thereof. In some embodiments, the genetically modified non-human animal is heterozygous for the engineered IgH allele. In some embodiments, the genetically modified non-human animal is homozygous for the engineered IgH allele. In some embodiments, the genetically modified non-human animal does not express IgG molecules comprising light chains. In some embodiments, the genetically modified non-human animal does not express IgG molecules comprising light chains. In some embodiments, the engineered IgH allele does not comprise rearranged genes. In some embodiments, the engineered IgH allele does not comprise exogenous sequences, such as human or camelid V, D, or J genes. In some embodiments, the genetically modified non-human animal has a fully functional endogenous light chain locus. In some embodiments, the engineered IgH allele comprises a fully functional Cμ gene. In some embodiments, the genetically modified non-human animal expresses wildly pe IgM, IgA, IgD, and IgE proteins.

In some embodiments, there is provided a genetically modified non-human animal comprising a germline genome comprising an engineered immunoglobulin heavy chain (IgH) allele at an endogenous IgH locus, wherein the engineered IgH allele comprises a defective splice site (such as a G(+1) to A (+1) transversion mutation) immediately after the CH1 exon of each endogenous Cγ gene. In some embodiments, the genetically modified non-human animal is heterozygous for the engineered NH allele. In some embodiments, the genetically modified non-human animal is homozygous for the engineered IgH allele. In some embodiments, the genetically modified non-human animal does not express IgG molecules comprising light chains. In some embodiments, the genetically modified non-human animal does not express IgG molecules comprising light chains. In some embodiments, the engineered IgH allele does not comprise rearranged genes. In some embodiments, the engineered IgH allele does not comprise exogenous sequences, such as human or camelid V, D, or J genes. In some embodiments, the genetically modified non-human animal has a fully functional endogenous light chain locus. In some embodiments, the engineered IgH allele comprises a fully functional Cμ gene. In some embodiments, the genetically modified non-human animal expresses wildtype IgM, IgA, IgD, and IgE, proteins.

In some embodiments, there is provided a genetically modified non-human animal comprising a germline genome comprising an engineered immunoglobulin heavy chain (IgH) allele at an endogenous IgH locus, wherein the engineered IgH allele lacks the CH1 exon of each endogenous Cγ gene. In some embodiments, the genetically modified non-human animal is heterozygous for the engineered IgH allele. In some embodiments, the genetically modified non-human animal is homozygous for the engineered IgH allele. In some embodiments, the (genetically modified non-human animal does not express IgG molecules comprising light chains. In some embodiments, the genetically modified non-human animal does not express IgG molecules comprising light chains. In some embodiments, the engineered IgH allele does not comprise rearranged genes. In some embodiments, the engineered IgH allele does not comprise exogenous sequences, such as human or camelid V, D, or J genes, in some embodiments, the genetically modified non-human animal has a fully functional endogenous light chain locus. In some embodiments, the engineered IgH allele comprises a fully functional Cμ gene. In some embodiments, the genetically modified non-human animal expresses wild-type IgM, IgA, IgD, and IgE proteins.

In some embodiments, there is provided a genetically modified non-human animal comprising a germline genome comprising an engineered immunoglobulin heavy chain (IgH) allele at an endogenous IgH locus, wherein the engineered IgH allele lacks all endogenous Cγ genes except for the CH2 and CH3 exons of the most downstream endogenous Cγ gene. In some embodiments, the genetically modified non-human animal is heterozygous for the engineered IgH allele. In some embodiments, the genetically modified non-human animal is homozygous for the engineered IgH allele. In some embodiments, the genetically modified non-human animal does not express IgG molecules comprising light chains. In some embodiments, the genetically modified non-human animal does not express IgG molecules comprising light chains. In some embodiments, the engineered IgH allele does not comprise rearranged genes. In some embodiments, the engineered IgH allele does not comprise exogenous sequences, such as human or camelid V, D, or J genes. In some embodiments, the genetically modified non-human animal has a fully functional endogenous light chain locus. In some embodiments, the engineered IgH allele comprises a fully functional Cμ gene. In some embodiments, the genetically modified non-human animal expresses wild-type IgA, IgD, and IgE proteins.

In some embodiments, the genetically modified non-human animal has fully functional heavy chain variable regions, including V, D, and J genes. In some embodiments, the genetically modified non-human animal has fully functional endogenous heavy chain variable regions, including V, D, and J genes. In some embodiments, the engineered IgH allele does not comprise rearranged genes, such as rearranged V, D, and J genes. In some embodiments, the engineered IgH allele comprises unrearranged V, D, and J genes. In some embodiments, the engineered IgH allele comprises the full set of unrearranged endogenous V, D, and J genes.

In some embodiments, the genetically modified non-human animal does not comprise exogenous heavy chain variable regions of a different species, such as human or camelid V, D, or J genes. In some embodiments, the engineered IgH allele comprises unaltered endogenous heavy chain variable regions. In some embodiments, the engineered IgH allele is not a chimeric IgH construct comprising heavy chain variable regions from a different species. In some embodiments, the engineered IgH allele does not comprise human V, D, or J genes. In some embodiments, the engineered IgH allele does not comprise camelid V, D, or J genes. In some embodiments, the engineered IgH allele does not comprise genes derived from a naturally occurring locus, such as a Camelid VHH locus.

In some embodiments, the genetically modified non-human animal does not comprise any exogenous sequence in its germline genome, such as human or camelid IgH gene fragments. In some embodiments, the genetically modified non-human animal does not comprise human V, D, or J gene segments in its germline genome. In some embodiments, the genetically modified non-human animal does not comprise camelid V, D, or J gene segments in its germline genome. In some embodiments, the genetically modified non-human animals does not comprise any genes encoding humanized or camelized variable regions, such as rearranged or unrearranged genes that give rise to CDRs or FRs that have human or camelid characteristics or sequences. In some embodiments, the genetically modified non-human animal does not comprise genes encoding human constant regions, such as human hinge, CH2 anchor CH3 regions.

In some embodiments, the engineered IgH allele does not comprise an exogenous sequence, such as a recombination site, or a homologous arm to facilitate insertion of exogenous sequences into the genome. In some embodiments, the engineered IgH allele does not comprise a reporter gene, such as fluorescence reporter or antibiotic resistance gene for selecting engineered cells. In some embodiments, the engineered IgH allele comprises random nucleotides introduced by non-homologous end joining. In some embodiments, the engineered IgH allele does not comprise an exogenous sequence other than random insertions and deletions introduced by DNA repair.

In some embodiments, the engineered IgH allele comprises one or more exogenous sequences. In some embodiments, the engineered IgH allele comprises a reporter gene, such as fluorescence reporter or antibiotic resistance gene for selecting engineered cells. In some embodiments, the engineered IgH allele comprises recombination sites or homologous arms to facilitate insertion of exogenous sequences into the genome.

In some embodiments, the engineered IgH allele only has modifications to the CH1 exon of Cγ genes. In some embodiments, the modification does not comprise a mutation, such as deletion or loss-of-function mutation, of a gene encoding a hinge region of the IgG. In some embodiments, the modification does not comprise a mutation, such as deletion or loss-of-function mutation to the CH2 or the CH3 exons of the Cγ genes. In some embodiments, the engineered IgH allele does not have mutations or modifications to the CH1 exon of a Cμ gene. In some embodiments, the genetically modified non-human animal has a functional gene segment encoding CH1 of IgM at the endogenous IgH locus.

In some embodiments, the genetically modified non-human animal has fully functional genes encoding other heavy chain constant isotypes, such as IgM, IgD, IgE, and/or IgA. In some embodiments, the genetically modified non-human animal has fully functional Cμ, Cδ, Cε and/or Cα genes. In some embodiments, the engineered IgH allele has wildtype Cμ, Cδ, Cε and/or Cα genes. In some embodiments, the engineered IgH allele does not comprise any mutation to the endogenous Cμ, Cδ, Cε and/or Cα genes. In some embodiments, the genetically modified non-human animal has a fully functional, such as a wildtype, Cμ gene. In some embodiments, the endogenous IgH locus has an intact endogenous Cμ gene. In some embodiments, the genetically modified non-human animal has fully functional, such as wildtype Cμ, Cδ, Cε and Cα genes. In some embodiments, the genetically modified non-human animal expresses wildtype IgM, IgD, IgA, and IgE proteins.

In some embodiments, introduction of minimal changes to the endogenous IgH locus in the genetically modified non-human animal promotes health of the animal, including normal B cell development and maturation. In some embodiments, introduction of minimal changes to the endogenous IgH locus in the genetically modified non-human animal reduces or avoids immunogenicity of exogenous sequences to the animal. In some embodiments, introduction of minimal changes to the endogenous IgH locus in the genetically modified non-human animal preserves the normal functions of the endogenous IgH locus, including V-D-J recombination, classic switch recombination (CSR), and somatic hypermutation.

In some embodiments, the genetically modified non-human animal has one or more fully functional light chain loci, such as λ light chain locus, and/or κ light chain locus. In some embodiments, the genetically modified non-human animal has an unaltered endogenous light chain locus. In some embodiments, no mutations are introduced to the endogenous light chain loci of the genetically modified non-human animal. In some embodiments, the lambda and/or kappa light chain variable region locus of the genetically modified non-human animal is functional, not silenced. In some embodiments, the genetically modified non-human animal expresses a wildtype λ light chain, and/or wildtype κ light chain. In some embodiments, the genetically modified non-human animal expresses functional molecules comprising light chains. In some embodiments, the genetically modified non-human animal expresses functional IgA, IgD, and/or IgE molecules comprising light chains. In some embodiments, the genetically modified non-human animal does not have an exogenous light chain gene or gene cluster.

Previously made genetically modified animals that can produce heavy chain-only antibodies differ from the genetically modified animals described herein in many ways. Some transgenic animals were made by mimicking the IgH loci in species that naturally make HcAbs, e.g., camelids and certain fish. For example, transgenic animals were made that lacked the CH1 exons in the constant region genes encoding both IgMs and IgGs, while camelid, or camelized VHH or VHH-like heavy chain variable regions or human heavy chain variable genes were introduced to the engineered IgH loci. The deletion of IgM and IgG CH1 domains was undertaken presumably to prevent formation of endogenous, natural antibodies to compete with camelized antibody formation from a genetically modified IgH locus. The addition of VHH gene segments was undertaken presumably to mimic heavy chain antibody formation in combination with the CH1 deletion. In other studies, exogenous IgH locus constructs were introduced to the genome of transgenic non-human animals. Human or camelid V, D, and J genes were combined with murine heavy chain constant region genes that were engineered to delete one or more CH1 exons. See, for example, U.S. Pat. No. 8,754,287. Another approach relies upon the absence of functional kappa or lambda gene segments that can rearrange to form a functional light chain gene, and on the absence of any functional rearranged light chain gene. Large amount of RNAs encoding the heavy chain comprising CH1 domains was made by these light chain deficient animals. None of the genetically engineered animals known to date can produce exclusively heavy chain-only IgG molecules with full set of endogenous heavy chain variable repertoire, while keeping the B cell development and maturation processes in the animals undisturbed.

The genetically modified non-human animal can be of any suitable species for antibody production. In some embodiments, the genetically modified non-human animal is a mammal, including, but not limited to, rodents, simians, felines, canines, equines, bovines, porcines, ovines, caprines, mammalian laboratory animals, mammalian farm animals, mammalian sport animals, and mammalian pets. In some embodiments, the genetically modified non-human animal is a rodent. In some embodiments, t e genetically modified non-human animal is a mouse. In some embodiments, the genetically modified mouse is an inbred mouse. In some embodiments, the genetically modified mouse is an outbred mouse. In some embodiments, the genetically modified mouse is of the C57BL/6J strain, the 129S1/SvImJ strain, BALB/c strain, CBA/J strain, DBA/2J strain, C3H.SW (H-2b) strain, NOD/ShiLtJ strain, AKR/J (AKR) strain, A/J, FvB/NJ strain, C3H/HeJ (C3H) strain, B6 strain, ICR strain, C58/J (C58) strain, CBA/J strain or MRL/Mpl strain. Other suitable inbred strains and outbred strains include, but are not limited to CD-1 strain, Swiss Webster. In some embodiments, the genetically modified non-human animal is a rat. In some embodiments, the genetically modified non-human animal is a rabbit.

Different animal species have different germline organization and genes at their endogenous immunoglobulin heavy chain (IgH) loci. The IgH loci of many species have been sequenced. The gene positions and exon/intron organization of the IgH loci in mouse, rat and rabbit can be found, for example, at worldwide web.imgt.org/IMGTrepertoire/LocusGenes.

For example, the endogenous IgH locus of mouse spans about 2.3 Mb on chromosome 12 (12F2) in the mouse reference genome. In inbred mouse having the IGH1-b allele, there are four IgG subclasses, including IgG3, IgG1, IgG2b and IgG2c, the constant regions of which are encoded by Cγ3, Cγ1, Cγ2b and Cγ2c respectively. The order of the IgG constant region genes in the endogenous IgH locus from the most upstream to the most downstream is as follows: Cγ3, Cγ1, Cγ2b and Cγ2c. Other mouse strains produce IgG2a subclass molecules instead of the IgG2c subclass, and the heavy chain region of the IgG2a subclass is encoded by the Cγ2a gene. Each Cγ gene comprises from the 5' to the 3': a 5' UTR, a CH1 exon, an intron, a hinge (H) exon, an intron, a CH2 exon, an intron, a CH3 exon (or CH3-CHS exon), an intron, the stop codon, and polyA signal. An acceptor splice site is located immediately upstream (5') to each exon, and a donor splice site is located immediately downstream (3') to each exon. The intergenic fragments in the endogenous site between each Cγ gene of the mouse IgH locus in C57BL/6J strain is as follows: Cγ3-34 kb-Cγ1-21 kb-Cγ2b-15 kb-Cγ2c. The endogenous gene segment encompassing Cγ3, Cγ1, Cγ2b and the CH1 exon of Cγ2c is about 72.7 kb. It has been technically challenging to delete such a large endogenous fragment from the mouse genome, and the effects for deleting a 72.7 kb fragment from the mouse genome are unpredictable.

In some embodiments, the genetically modified mouse comprises an engineered IgH allele at an endogenous IgH locus, wherein the engineered IgH allele lacks a functional gene segment encoding each CH1 exon of Cγ3, Cγ1, Cγ2b and Cγ2c/Cγ2a. In some embodiments, the engineered IgH allele comprises a defective splice site (such as a G(+1) to A(+1) transversion mutation) immediately after the CH1 exon of Cγ3, Cγ1, Cγ2b, and/or Cγ2c/Cγ2a. In some embodiments, the engineered IgH allele lacks the CH1 exon of Cγ3, Cγ1, Cγ2b, and/or Cγ2c/Cγ2a. In some embodiments, the engineered IgH allele lacks the Cγ3, Cγ1, and/or Cγ2b gene. In some embodiments, the engineered IgH allele lacks an endogenous gene segment comprising Cγ3, Cγ1, Cγ2b and CH1 exon of Cγ2c/Cγ2a, which is about 72.7 kb long. In some embodiments, the engineered IgH allele comprises a nucleotide sequence of no more than about 500 nucleotides (such as no more than about any one of 400, 300, 250, 200, 150, 100, 75, or 50 nucleotides) long, and wherein the nucleotide sequence comprises SEQ ID NO: 27 (TATCCTACATGCTCTTTGCAGAAC) and SEQ ID NO: 28 (AGACCAGCCAGGATGAGCAGCCAT). In some embodiments, the engineered IgH comprises a nucleotide sequence selected from SEQ ID NOs: 1-25. In some embodiments, the genetically modified mouse comprises the full intact endogenous mouse heavy chain immunoglobulin variable region genes, including about 150-170 IGHV genes, 17-20 IGHD genes and 4 IGHJ genes.

In some embodiments, there is provided a genetically modified mouse comprising a germline genome comprising an engineered IgH allele at an endogenous IgH locus, wherein the engineered IgH allele lacks an endogenous gene segment comprising Cγ3, Cγ1, Cγ2b and CH1 exon of Cγ2c. In some embodiments, the engineered IgH allele comprises a nucleotide sequence of no more than about 250 nucleotides (such as no more than about 200, or 100 nucleotides) long, and wherein the nucleotide sequence comprises SEQ ID NO: 27 and SEQ ID NO: 28. In some embodiments, the engineered IgH allele comprises a nucleotide sequence selected from SEQ ID NOs: 1-25. In some embodiments, the genetically modified mouse is heterozygous for the engineered IgH allele. In some embodiments, the genetically modified mouse is homozygous for the engineered IgH allele. In some embodiments, the genetically modified mouse does not express IgG molecules comprising light chains. In some embodiments, the engineered IgH allele does not comprise rearranged genes. In some embodiments, the engineered IgH allele does not comprise exogenous sequences, such as human or camelid V, D, or J genes. In some embodiments, the genetically modified mouse has a fully functional endogenous light chain locus. In some embodiments, the engineered IgH allele comprises a fully functional Cμ gene. In some embodiments, the genetically modified mouse expresses wildly pe IgM, IgA, IgD, and IgE proteins.

The endogenous IgH locus of rat is located on chromosome 6q32-33 spanning about 4.9 Mb in the *Rattus norvegicus* genome. Rats express four IgG subclasses, including IgG2c, IgG2a, IgG1 and IgG2b, the constant regions of which are encoded by Cγ2c, Cγ2a, Cγ1 and Cγ2b respectively. The order of the IgG constant region genes in the endogenous IgH locus from the most upstream to the most downstream is as follows: Cγ2c, Cγ2a, Cγ1 and Cγ2b. The endogenous gene segment encompassing Cγ2c, Cγ2a, Cγ1 and the CH1 exon of Cγ2b is about 140 kb.

In some embodiments, the genetically modified rat comprises an engineered IgH allele at an endogenous IgH locus, wherein the engineered IgH allele lacks a functional gene segment encoding each CH1 exon of Cγ2c, Cγ2a, Cγ1 and Cγ2b. In some embodiments, the engineered IgH allele comprises a defective splice site (such as a G(+1) to A(+1) transversion mutation) immediately after the CH1 exon of Cγ2c, Cγ2a, Cγ1 and/or Cγ2b. In some embodiments, the engineered IgH allele lacks the CH1 exon of Cγ2c, Cγ2a, Cγ1 and/or Cγ2b. In some embodiments, the engineered IgH allele lacks the Cγ2c, Cγ2a, and/or Cγ1 gene. In some embodiments, the engineered IgH allele lacks an endogenous gene segment comprising Cγ2c, Cγ2a, Cγ1 and the CH1 exon of Cγ2b. In some embodiments, the genetically modified rat comprises the full intact endogenous rat heavy chain immunoglobulin variable region genes, including about 350 IGHV genes, 20 IGHD genes and 5 IGHJ genes.

In some embodiments, there is provided a genetically modified rat comprising a germline genome comprising an engineered IgH allele at an endogenous IgH locus, wherein the engineered IgH allele lacks an endogenous gene segment comprising Cγ2c, Cγ2a, Cγ1 and the CH1 exon of Cγ2b. In some embodiments, the genetically modified rat is heterozygous for the engineered IgH allele. In some embodiments, the genetically modified rat is homozygous for the engineered IgH allele. In some embodiments, the genetically modified rat does not express IgG molecules comprising light chains, in some embodiments, the engineered IgH allele does not comprise rearranged genes. In some embodiments, the engineered IgH allele does not comprise exogenous sequences, such as human or camelid V, D, or J genes. In some embodiments, the genetically modified rat has a fully functional endogenous light chain locus. In some embodiments, the engineered IgH allele comprises a fully functional Cu gene. In some embodiments, the genetically modified rat expresses wildtype IgM, IgA, IgD, and IgE proteins.

The endogenous IgH locus of rabbit is located on chromosome 20 in the *Orytolagus cuniculus* genome. Rabbits express a single IgG subclass, the constant region of which is encoded by the Cγ gene.

In some embodiments, there is provided a genetically modified rabbit comprising a germline genome comprising an engineered IgH allele at an endogenous IgH locus, wherein the engineered IgH allele lacks the endogenous CH1 exon of Cγ. In some embodiments, there is provided a genetically modified rabbit comprising a germline genome comprising an engineered IgH allele at an endogenous IgH locus, wherein the engineered IgH allele comprises a defective splice site (such as G(+1) to A(+1) transversion mutation) immediately after the CH1 exon of Cγ. In some embodiments, the genetically modified rabbit is heterozygous for the engineered IgH allele. In some embodiments, the genetically modified rabbit is homozygous for the engineered IgH allele. In some embodiments, the genetically modified rabbit does not express IgG molecules comprising light chains. In some embodiments, the engineered IgH allele does not comprise rearranged genes. In some embodiments, the engineered IgH allele does not comprise exogenous sequences, such as human or camelid V, D, or genes. In some embodiments, the genetically modified rabbit has a fully functional endogenous light chain locus. In some embodiments, the engineered IgH allele comprises a fully functional Cμ gene. In some embodiments, the genetically modified rabbit expresses wildtype IgA, IgD, and IgE proteins.

The genetically modified non-human animals can be made using any known genome-editing methods in the art, including, but not limited to, homologous recombination methods, or using sequence-specific endonucleases, including, but not limited to, CRISPR/cas, Zinc-finger nuclease (ZFN), TALEN genome editing methods, and meganucleases. In some embodiments, the genetically modified non-human animal is produced by CRISPR/Cas zygote genome editing methods. In some embodiments, the genetically modified non-human animal is produced by deleting an endogenous gene segment from the endogenous IgH locus using CRISPR/Cas genome editing methods.

Genome editing can be carried out in isolated embryonic stem (ES) cells, or in embryos. For example, a customized sequence-specific endonuclease system, such as CRISPR/cas, ZFN, TALEN or meganuclease can be injected into the ES cell or embryo (e.g. a one cell embryo) in vitro to initiate the genome editing. A donor nucleic acid that may be integrated at the cleaved target locus may also be injected into the ES cell or embryo at the same time. The donor nucleic acid may comprise an engineered allele. Clones of the ES cell may be employed as donor ES cells in an embryo of the non-human animal wider conditions suitable for making an ES cell-derived mouse. Optionally, genetically modified ES cell or genetically modified ES embryo may be selected using a reporter gene or selection marker. The genetically modified embryo can be implanted into a surrogate animal to produce founder offspring. The founder offspring may be screened using known methods in the art, such as PCR and sequencing of the IgH locus, to select for successfully modified non-human animals that have an engineered IgH allele. The founder offspring may be further bred to produce genetically modified non-human animals that are homologous for the engineered IgH allele.

The CRISPR/Cas (Clustered Regularly interspaced Short Palindromic Repeats) system exploits RNA-guided DNA-binding and sequence-specific cleavage of target DNA. A guide RNA (gRNA) contains about 20-25 (such as 20) nucleotides that are complementary to a target genomic DNA sequence upstream of a genomic PAM (protospacer adjacent motifs) site and a constant RNA scaffold region. In certain embodiments, the target sequence is associated with a PAM, which is a short sequence recognized by the CRISPR complex. The precise sequence and length requirements for the PAM differ depending on the CRISPR enzyme used, but PAMs are typically 2-5 bp sequences adjacent to the protospacer (that is, the target sequence). Examples of PAM sequences are known in the art, and the skilled person will be able to identify further PAM sequences for use with a given CRISPR enzyme. For example, target sites for Cas9 from *S. pyogenes*, with PAM sequences NGG, may be identified by searching for 5'-Nx-NGG-3' both on an input sequence and on the reverse-complement of the input. In certain embodiments, the genomic PAM site used herein is NGG, NNG, NAG, NGGNG, or NNAGAAW. Other PAM sequences and methods for identifying PAM sequences are known in the art, for example, as disclosed in U.S. Pat. No. 8,697,359, the disclosure of which is incorporated herein by reference for all purposes. An exemplary type II CRISPR system is the type II CRISPR locus from *Streptococcus pyogenes* SF370, which contains a cluster of four genes Cas9, Cas1, Cas2, and Csn1, as well as two non-coding RNA elements, tracrRNA and a characteristic array of repetitive sequences (direct repeats) interspaced by short stretches of non-repetitive sequences (spacers, about 30 bp each). In some embodiments, the *Streptococcus pyogenes* Cas9 (SpCas9) is used and the corresponding PAM is NGG. In some aspects, different Cas9 enzymes from different bacterial strains use different PAM sequences. Suitable targets for modification (such as deletion or substitution) can be identified based on the sequence of endogenous IgH loci in the non-human animal. The corresponding gRNAs can be designed using known methods in the art.

The Cas (CRISPR-associated) protein binds to the gRNA and the target DNA to which the gRNA binds and introduces a double-strand break in a defined location upstream of the PAM site. The CRISPR-Cas systems have been used for editing, regulating and targeting genomes, for example, as disclosed in Sander and Joung, 2014 Nature Biotechnology 32(4): 347-55. Additional descriptions of CRISPR and/or Cas and methods of use can be found in WO 2007025097, US 20100093617, US 20130011828, U.S. Ser. No. 13/960,796, U.S. Pat. No. 8,546,553, WO 2010011961, US 20140093941, US 20100076057, US 20110217739, WO 2010075424, WO 2013142578, WO 2013141680, US 20130326645, WO 2013169802, US 20140068797, WO 2013176772, WO 2013181440, US 20130330778, WO 2013188037, WO 2013188522, WO 2013188638, WO 2013192278, WO 2014018423, CN 103388006, WO 2014022702, US 20140090113, WO 2014039872, WO 2014065596, U.S. Pat. No. 8,697,359, and CN 103725710, the disclosures of which are incorporated herein by reference in their entireties for all purposes.

ZFNs are recombinant proteins composed of DNA-binding zinc finger protein domains and effector nuclease domains. Zinc finger protein domains are ubiquitous protein domains, e.g., associated with transcription factors, that recognize and bind to specific DNA sequences. One of the "finger" domains can be composed of about thirty amino acids that include invariant histidine residues in complex with zinc. While over 10,000 zinc finger sequences have been identified thus far, the repertoire of zinc finger proteins has been further expanded by targeted amino acid substitutions in the zinc finger domains to create new zinc finger proteins designed to recognize a specific nucleotide sequence of interest. For example, phage display libraries have been used to screen zinc finger combinatorial libraries for desired sequence specificity (Rebar et al., Science 263: 671-673 (1994); Jameson et al, Biochemistry 33:5689-5695 (1994); Choo et al., PNAS 91: 11163-11167 (1994), each of which is incorporated herein as if set forth in its entirety). Zinc finger proteins with the desired sequence specificity can then be linked to an effector nuclease domain, e.g., as described in U.S. Pat. No. 6,824,978, such as FokI, described in PCT Application Publication Nos. WO1995/09233 and WO1994018313.

Transcription activator-like effector endonucleases (TALEN) comprise a TAL effector domain that binds to a specific nucleotide sequence and an endonuclease domain that catalyzes a double-strand break at the target site. Examples of TALENs and methods of making and using are described by PCT Patent Application Publication Nos. WO2011072246 and WO 2013163628, and U.S. Application Publication No. US 20140073015 A1. TALENs may be used to introduce site-specific double-strand breaks at targeted genomic loci. Site-specific double-strand breaks are created when two independent TALENs bind to nearby DNA sequences, thereby permitting dimerization of FokI and cleavage of the target DNA. TALENs have advanced genome editing due to their high rate of successful and efficient genetic modification. This DNA cleavage may stimulate the natural DNA-repair machinery, leading to one of two possible repair pathways: homology-directed repair (HDR) or the non-homologous end joining (NHEJ) pathway. The TALENs may be designed to target any gene, including genes involved in a genetic disease.

In some embodiments, the genetically modified non-human animal is produced by introducing one or more loss-of-functional imitations to endogenous gene segments encoding the CH1 domains of all endogenous IgG subclasses at an endogenous IgH locus in the germline genome of a non-human animal. In some embodiments, the one or more mutations comprise a loss-of-function mutation (such as G(+1) to A(+1) transversion mutation) to the splice site immediately after the CH1 exon of a Cγ gene. In some embodiments, the one or more mutations comprise deletion of a Cγ gene or the CH1 exon of a Cγ gene. In some embodiments, the one or more mutations are introduced to the endogenous IgH locus of the non-human animal sequentially. In some embodiments, an endogenous gene segment comprising all Cγ genes except for the CH2 and CH3 exons of the most downstream Cγ gene is deleted from the endogenous IgH locus. In some embodiments, the one or more mutations comprise a combination of imitation to the splice site immediately after the CH1 exon of a Cγ gene, deletion of a Cγ gene, and deletion of the CH1 exon of a Cγ gene.

Thus, in some embodiments, there is provided a method of producing a genetically modified non-human animal capable of producing heavy chain-only antibodies (HcAbs), comprising introducing one or more loss-of-function mutations to gene segments encoding the CH1 domains of all endogenous IgG subclasses at an endogenous immunoglobulin heavy chain (IgH) locus in the germline genome of a non-human animal, thereby providing the genetically modified non-human animal. In some embodiments, the one or more mutations is selected from the group consisting of a loss-of-function mutation to the splice site immediately after the CH1 exon of a Cγ gene, deletion of a Cγ gene, deletion of the CH1 exon of a Cγ gene, and combinations thereof. In some embodiments, wherein the non-human animal is a mouse, the genetically modified non-human animal is produced by deleting an endogenous gene segment comprising Cγ3, Cγ1, Cγ2b and CH1 exon of Cγ2c from the endogenous IgH locus. In some embodiments, wherein the non-human animal is a rat, the genetically modified non-human animal is produced by deleting an endogenous gene segment comprising Cγ2c, Cγ2a, Cγ1 and the CH1 exon of Cγ2b. In some embodiments, wherein the non-human animal is a rabbit, the genetically modified non-human animal is produced by deleting the endogenous CH1 exon of Cγ. In some embodiments, the one or more mutations are introduced to the endogenous IgH locus by CRISPR/Cas9 genome editing.

In some embodiments, the one or more mutations are introduced to the endogenous IgH locus of the non-human animal by zygote genome editing. In some embodiments, the method comprises introducing the one or more mutations to the endogenous IgH locus in a one-cell embryo of a non-human animal, implanting the embryo in a surrogate animal, and breading the surrogate animal to produce the genetically modified non-human animal. In some embodiments, the method comprises injecting a sequence-specific endonuclease or a nucleic acid (e.g., mRNA or DNA) encoding the endonuclease, and any corresponding guide nucleic acid to the one-cell embryo to initiate genome editing.

In some embodiments, there is provided a method of producing a genetically modified non-human animal capable of producing heavy chain-only antibodies (HcAb), comprising injecting an mRNA encoding Cas 9, a first sgRNA targeting the first intron or 5'UTR upstream of the CH1 exon of the first Cγ gene in the endogenous IgH locus, and a second sgRNA targeting the first intron downstream of the CH1 exon of the last Cγ gene in the endogenous IgH locus into a one-cell embryo of a non-human animal, implanting the embryo into a surrogate animal, and breeding the surrogate animal to produce the genetically modified non-human animal. In some embodiments, wherein the non-human animal is a mouse, the first Cγ gene is Cγ3, and the last Cγ gene is Cγ2c (or Cγ2a). In some embodiments, wherein the non-human animal is a rat, the first Cγ gene is Cγ2c, and the last Cγ gene is Cγ2b. In some embodiments, Wherein the non-human animal is a rabbit, the method comprises injecting an mRNA encoding Cas 9, a first sgRNA targeting the first intron or 5'UTR upstream of the CH1 exon of Cγ gene in the endogenous IgH locus, and a second sgRNA targeting the first intron downstream of the CH1 exon of Cγ gene in the endogenous IgH locus into a one-cell embryo of a rabbit.

Genetically modified non-human animals produced using any of the methods described herein are provided. Compositions, gRNAs, and engineered IgH allele constructs for use in the methods of producing genetically modified non-human animals are also provided.

The genetically modified non-human animals described herein have one or more of the following characteristics: (1) the genetically modified non-human animal expresses a plurality of IgG proteins in response to an antigen, wherein the plurality of IgG proteins do not contain light chains; (2) the genetically modified non-human animal is fertile; (3) the genetically modified non-human animal has substantially normal B cell development and maturation; and (4) the genetically modified non-human animal has substantially normal V-D-J recombination, substantially normal classic switch recombination (CSR), and substantially normal somatic hypermutations.

IgG molecules can be characterized using various methods known in the art, including, for example, size-exclusion chromatography, dynamic light scattering, and SDS-PAGE electrophoresis analysis under non-reducing or reducing conditions. Heavy-chain only IgG molecules do not have light chains, and thus are smaller in size than conventional IgG molecules having both heavy chains and light chains. Light chains can be detected by Western blotting or ELISA.

Fertility of animals can be determined by counting brood size. Immunological health and development of the genetically modified non-human animals can be determined using known methods in the art. B-cell development and maturation can also be assessed using methods such as flow cytometry analysis, immunohistochemistry, ELISA, Western blotting, or PCR detection using bone marrow, spleen and/or blood samples. B cells at different stages of development are characterized by their cell surface biomarkers. For example, pro-B cells in mice are c-kit⁺B22⁺, pre-B cells are CD43⁺B220⁺, immature B cells are B220⁺CD43⁻, and mature B cells are CD21/35⁺. Other useful cell markers for assessment of B cell development include, but are not limited to, CD138 and CD19. V-D-J recombination, classic switch recombination (CSR), and somatic hypermutation can be detected and assessed by RT-PCR using RNA samples from mature antibody-producing B cells.

Further provided herein are genetically modified cells and non-human embryos. In some embodiments, there is provided a genetically modified non-human cell comprising a genome comprising an engineered immunoglobulin heavy chain (IgH) allele at an endogenous IgH locus, wherein the engineered IgH allele lacks functional endogenous gene segments encoding CH1 domains of all endogenous IgG subclasses. In some embodiments, the cell is selected from a non-human embryonic stem (ES) cell, a pluripotent cell, a totipotent cell or an iPS cell. In some embodiments, the cell is selected from a mouse ES cell, a rat ES cell, or a rabbit ES cell.

In some embodiments, there is provided a genetically modified non-human embryo comprising a genome comprising an engineered immunoglobulin heavy chain (IgH) allele at an endogenous NH locus, wherein the engineered IgH allele lacks functional endogenous gene segments encoding CH1 domains of all endogenous IgG subclasses. In some embodiments, the non-human embryo is at the one-cell stage. In some embodiments, the non-human embryo is a mouse embryo, a rat embryo, or a rabbit embryo.

In some embodiments, there is provided a non-human embryo comprising a genetically modified donor cell, comprising a genome comprising an engineered immunoglobulin heavy chain (IgH) allele at an endogenous IgH locus, wherein the engineered IgH allele lacks functional endogenous gene segments encoding CH1 domains of all endogenous IgG subclasses. In some embodiments, the non-human embryo is a mouse embryo, a rat embryo, or a rabbit embryo, and the donor cell is a mouse ES cell, a rat ES cell, or a rabbit ES cell respectively.

III. Methods of Producing Heavy Chain-Only Antibodies

The present application also provides methods of producing heavy chain-only antibodies using any one of the genetically modified non-human animals described herein.

In some embodiments, there is provided a method of producing a heavy chain-only antibody (HcAb) that specifically binds to an antigen of interest, comprising: (a) immunizing a genetically modified non-human animal with the antigen, wherein the genetically modified non-human animal comprises a germline genome comprising an engineered immunoglobulin heavy chain (IgH) allele at an endogenous IgH locus, wherein the engineered IgH allele lacks functional endogenous gene segments encoding CH1 domains of all endogenous IgG subclasses; and (b) obtaining a HcAb that specifically hinds to the antigen from the immunized genetically modified non-human animal, thereby producing the HcAb. In some embodiments, the engineered IgH allele comprises one or more mutations selected from deletion of the CH1 exon of an endogenous Cγ gene, deletion of an endogenous Cγ gene, a mutation to the splice site immediately after the CH1 exon of an endogenous Cγ gene that leads to loss of the CH1 exon in mRNA transcripts of the Cγ gene, and combinations thereof. In some embodiments, the genetically modified non-human animal is homozygous for the engineered IgH allele. In some embodiments, the genetically modified non-human animal does not express IgG molecules comprising light chains. In some embodiments, the engineered IgH allele does not comprise rearranged genes. In some embodiments, the engineered IgH allele does not comprise exogenous sequences, such as human or camelid V, D, or J genes. In some embodiments, the genetically modified non-human animal has a fully functional endogenous light chain locus.

In some embodiments, there is provided a method of producing a heavy chain only antibody that specifically binds to an antigen of interest, comprising: (a) immunizing a genetically modified mouse with the antigen, wherein the genetically modified mouse comprises a germline genome comprising an engineered immunoglobulin heavy chain (IgH) allele at an endogenous IgH locus, wherein the engineered IgH allele lacks an endogenous gene segment comprising Cγ3, Cγ1, Cγ2b and CH1 exon of Cγ2c; and (b) obtaining a HcAb that specifically binds to the antigen from the immunized genetically modified non-human animal, thereby producing the HcAb. In some embodiments, the engineered IgH allele comprises a nucleotide sequence of no more than about 250 nucleotides (such as no more than about 209, or 100 nucleotides) long, and wherein the nucleotide sequence comprises SEQ ID NO: 27 and SEQ ID NO: 28. In some embodiments, the genetically modified mouse is homozygous for the engineered IgH allele. In some embodiments, the genetically modified mouse does not express IgG molecules comprising light chains. In some embodiments, the engineered IgH allele does not comprise rearranged genes. In some embodiments, the engineered IgH allele does not comprise exogenous sequences, such as human or camelid V, D, or J genes. In some embodiments, the genetically modified mouse has a fully functional endogenous light chain locus.

In some embodiments, there is provided a method of producing a heavy chain only antibody that specifically binds to an antigen of interest, comprising: (a) immunizing a genetically modified rat with the antigen, wherein the genetically modified rat comprises a germline genome comprising an engineered immunoglobulin heavy chain (IgH) allele at an endogenous IgH locus, wherein the engineered IgH allele lacks an endogenous gene segment comprising Cγ2c, Cγ2a, Cγ1 and the CH1 exon of Cγ2b; and (b) obtaining a HcAb that specifically binds to the antigen from the immunized genetically modified non-human animal, thereby producing the HcAb. In some embodiments, the genetically modified rat is homozygous for the engineered IgH allele. In some embodiments, the genetically modified rat does not express IgG molecules comprising light chains. In some embodiments, the engineered IgH allele does not comprise rearranged genes. In some embodiments, the engineered NH allele does not comprise exogenous sequences, such as human or camelid V, D, or J genes. In some embodiments, the genetically modified rat has a fully functional endogenous light chain locus.

In some embodiments, there is provided a method of producing a heavy chain only antibody that specifically binds to an antigen of interest, comprising: (a) immunizing a genetically modified rabbit with the antigen, wherein the genetically modified rabbit comprises a germline genome comprising an engineered immunoglobulin heavy chain (IgH) allele at an endogenous IgH locus, wherein the engineered IgH allele lacks the endogenous CH1 exon of Cγ; and (b) obtaining a HcAb that specifically binds to the antigen from the immunized genetically modified non-human animal, thereby producing the HcAb. In some embodiments, the genetically modified rabbit is homozygous for the engineered IgH allele. In some embodiments, the genetically modified rabbit does not express IgG molecules comprising light chains. In some embodiments, the engineered IgH allele does not comprise rearranged genes. In some embodiments, the engineered IgH allele does not comprise exogenous sequences, such as human or camelid V, D, or J genes. In some embodiments, the genetically modified rabbit has a fully functional endogenous light chain locus.

The HcAbs obtained from the genetically modified non-human animal can be monoclonal or polyclonal. In some embodiments, the HcAbs obtained from the genetically modified non-human animals are subject to further selection, affinity maturation, and/or engineering. In some embodiments, the method comprises: (i) obtaining a cell comprising a nucleic acid encoding the heavy chain of the HcAb; (ii) obtaining the nucleic acid from the cell; and (iii) expressing the nucleic acid in a host cell to provide the HcAb. In some embodiments, the nucleic acid is engineered to provide a derivative of the HcAb, such as a chimeric HcAb based on the CDR sequences of the HcAb, antigen-binding fragments of the HcAb, or fusion proteins comprising the HcAb or antigen-binding fragment thereof.

Exemplary derivatives of the HcAb include, but are not limited to, a bispecific constructs comprising the VH domains of two HcAbs that specifically bind to two epitopes of a single target antigen; a bispecific constructs comprising VH domains of two HcAbs binding to two different target antigens; a tri-, or multiple-specific construct comprising VH domains of three or more HcAbs that target three different target epitopes or antigens; a fusion construct comprising VH domains of HcAbs fused to other functional proteins, e.g. hormones, cytokines, growth factors, coagulation/clotting factors, enzymes, toxins, chemokines, antibodies, antibody fragments, and other scaffolds, fluorescence proteins, transcription factors, cell receptors, chimeric antigen receptors (CAR), T cell receptors, B cell receptors, NK cell receptors, macrophage receptors, check point inhibitors, and peptides etc.; a HcAb conjugate comprising a HcAb or VH of a HcAb conjugated to proteins, peptides, small molecules, drugs, etc.; a particle or nanoparticle comprising conjugated HcAbs or VH of HcAbs with other organic materials; and a gene therapy vector construct comprising a HcAb, a VH domain of a HcAb, or fusion proteins thereof.

Also provided herein are HcAbs produced by the methods described herein, HcAbs isolated from the genetically modified non-human animals described herein, derivatives of the HcAbs (such as fusion proteins and antigen-binding fragments), as well as compositions, kits and articles of manufacture for carrying out any one of the methods described herein. The HcAbs and derivatives thereof may be useful for a variety of applications, including serving as therapeutics for treating human diseases and conditions.

Monoclonal HcAbs

Monoclonal antibodies are obtained from a population of substantially homogeneous antibodies, i.e., the individual antibodies comprising the population are identical except for possible naturally occurring mutations and/or post-translational modifications (e.g., isomerizations, amidations) that may be present in minor amounts. For example, the monoclonal antibodies may be made using the hybridoma method first described by Kohler et al., *Nature,* 256:495 (1975), or may be made by recombinant DNA methods (U.S. Pat. No. 4,816,567).

In the hybridoma method, a mouse or other appropriate host animal, such as a hamster, is immunized as hereinabove described to elicit lymphocytes that produce or are capable of producing antibodies that will specifically bind the protein used for immunization. Alternatively, lymphocytes may be immunized in vitro. Lymphocytes then are fused with myeloma cells using a suitable fusing agent, such as polyethylene glycol, to form a hybridoma cell (Goding, *Monoclonal Antibodies: Principles and Practice,* pp. 59-103 (Academic Press, 1986).

The immunizing agent will typically include the antigenic protein or a fusion variant thereof. Generally either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell. Goding, *Monoclonal Antibodies: Principles and Practice,* Academic Press (1986), pp. 59-103.

Immortalized cell lines are usually transformed mammalian cells, particularly myeloma cells of rodent, bovine and human origin. Usually, rat or mouse myeloma cell lines are employed. The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which are substances that prevent the growth of HGPRT-deficient cells.

Preferred immortalized myeloma cells are those that fuse efficiently, support stable high-level production of antibody by the selected antibody-producing cells, and are sensitive to a medium such as HAT medium. Among these, preferred are murine myeloma lines, such as those derived from MOPC-21 and MPC-11 mouse tumors available from the Salk Institute Cell Distribution Center, San Diego, Calif. USA, and SP-2 cells (and derivatives thereof, e.g., X63-Ag8-653) available from the American Type Culture Collection, Manassas, Va. USA. Human myeloma and mouse-human heteromyeloma cell lines also have been described for the production of human monoclonal antibodies (Kozbor, *J. Immunol.,* 133:3001 (1984); Brodeur et al., *Monoclonal Antibody Production Techniques and Applications,* pp. 51-63 (Marcel Dekker, Inc., New York, 1987)).

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunosorbent assay (ELISA).

The culture medium in which the hybridoma cells are cultured can be assayed for the presence of monoclonal antibodies directed against the desired antigen. Preferably, the binding affinity and specificity of the monoclonal antibody can be determined by immunoprecipitation or by an in vitro binding assay, such as radioimmunoassay (RIA) or enzyme-linked assay (ELISA). Such techniques and assays are known in the in art. For example, binding affinity may be determined by the Scatchard analysis of Munson et al., *Anal. Biochem.,* 107:220 (1980).

After hybridoma cells are identified that produce antibodies of the desired specificity, affinity, and/or activity, the clones may be subcloned by limiting dilution procedures and grown by standard methods (Goding, supra), Suitable culture media for this purpose include, for example, D-MEM or RPMI-1640 medium. In addition, the hybridoma cells may be grown in vivo as tumors in a mammal.

The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

Also provided here are B cells isolated from the genetically modified non-human animal described herein, and hybridomas produced based on the B cells.

Monoclonal antibodies may also be made by recombinant DNA methods, such as those described in U.S. Pat. No. 4,816,567, and as described above. DNA encoding the monoclonal antibodies is readily isolated and sequenced using conventional procedures (e.g., by using oligonucleotide probes that are capable of binding specifically to genes encoding the heavy and light chains of murine antibodies). The hybridoma cells serve as a preferred source of such DNA. Once isolated, the DNA may be placed into expression vectors, which are then transfected into host cells such as *E. coli* cells, simian COS cells, Chinese hamster ovary (CHO) cells, or myeloma cells that do not otherwise produce immunoglobulin protein, in order to synthesize monoclonal antibodies in such recombinant host cells. Review articles on recombinant expression in bacteria of DNA encoding the antibody include Skerra et al., *Curr. Opinion in Immunol.*, 5:256-262 (1993) and Pliickthun, *Immunol. Revs.* 130:151-188 (1992).

In order for some secreted proteins to express and secrete in large quantities, a leader sequence from a heterologous protein may be desirable, in some embodiments, employing heterologous leader sequences may be advantageous in that a resulting mature polypeptide may remain unaltered as the leader sequence is removed in the ER during the secretion process. The addition of a heterologous leader sequence may be required to express and secrete some proteins.

Certain exemplary leader sequence sequences are described, e.g., in the online Leader sequence Database maintained by the Department of Biochemistry, National University of Singapore. See Choo et al., *BMC Bioinformatics*, 6: 249 (2005); and PCT Publication No. WO 2006/081430.

Chimeric HcAbs

In some embodiments, chimeric antibodies based on the HcAb produced by the genetically modified non-human animal are produced. Certain chimeric antibodies are described, e.g., in U.S. Pat. No. 4,816,567; and Morrison et al., (1984) *Proc. Natl. Acad. Sci. USA*, 81: 6851-6855 (1984)). In some embodiments, a chimeric antibody comprises a non-human variable region (e.g., a variable region derived from a mouse, rat, or rabbit) and a human constant region. In some embodiments, a chimeric antibody is a "class switched" antibody in which the class or subclass has been changed from that of the parent antibody. Chimeric antibodies include antigen-binding fragments thereof.

In some embodiments, a chimeric antibody described herein comprises one or more human constant regions. In some embodiments, the human heavy chain constant region is of an isotype selected from IgA, IgG, and IgD. In some embodiments, a chimeric antibody described herein comprises a human IgG constant region. It may be desirable to modify the HcAbs from the genetically modified non-human animal with respect to Fc effector function, e.g., so as to modify (e.g., enhance or eliminate) antigen-dependent cell-mediated cytotoxicity (ADCC) and/or complement dependent cytotoxicity (CDC) of the antibody. In some embodiments, Fc effector function of the HcAb is reduced or eliminated. In some embodiments, when effector function is desirable, a chimeric antibody comprising a human IgG1 heavy chain constant region or a human IgG3 heavy chain constant region is produced. In some embodiments, when effector function is not desirable, a chimeric antibody comprising a human IgG4 or IgG2 heavy chain constant region is produced.

Humanized HcAbs

In some embodiments, humanized antibodies based on the HcAb produced by the genetically modified non-human animal are produced. Humanized antibodies are useful as therapeutic molecules because humanized antibodies reduce or eliminate the human immune response to non-human antibodies (such as the human anti-mouse antibody (HAMA) response), which can result in an immune response to an antibody therapeutic, and decreased effectiveness of the therapeutic.

In some embodiments, the HcAb produced from the genetically modified non-human animal is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from the HcAb, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HAIR residues are derived), e.g., to restore or improve antibody specificity or affinity.

Humanized antibodies and methods of making them are reviewed, e.g., in Almagro and Fransson, (2008) *Front. Biosci.* 13: 1619-1633, and are further described, e.g., in Riechmann et al., (1988) *Nature* 332:323-329; Queen et al., (1989) *Proc. Natl. Acad. Sci. USA* 86: 10029-10033; U.S. Pat. Nos. 5,821,337, 7,527,791, 6,982,321, and 7,087,409; Kashmiri et al., (2005) *Methods* 36:25-34 (describing SDR (a-CDR) grafting); Padlan, (1991) *Mol. Immunol.* 28:489-498 (describing "resurfacing"), Dall'Acqua et al., (2005) *Methods* 36:43-60 (describing "FR shuffling"); and Osbourn et al., (2005) *Methods* 36:61-68 and Klimka et al., (2000) *Br. J. Cancer*, 83:252-260 (describing the "guided selection" approach to FR shuffling).

Human framework regions that may be used for humanization include but are not limited to: framework regions selected using the "best-fit" method (see, e.g., Sims et al. (1993) *J. Immunol.* 151: 2296); framework regions derived from the consensus sequence of human antibodies of a particular subgroup of light or heavy chain variable regions (see, e.g., Carter et al. (1992) *Proc. Natl. Acad. Sci. USA*, 89:4285; and Presta et al. (1993) *J. Immunol*, 151:2623); human mature (somatically mutated) framework regions or human germline framework regions (see, e.g., Almagro and Fransson, (2008) *Front. Biosi.* 13:1619-1633); and framework regions derived from screening FR libraries (see, e.g., Baca et al., (1997) *J. Biol. Chem.* 272: 10678-10684 and Rosok et al., (1996) *J. Biol. Chem.* 271: 22611-22618).

Antibody Fragments

In some embodiments, antibody fragments based on the HcAb produced by the genetically modified non-human animal are produced. In certain circumstances there are advantages to using antibody fragments, such as antigen binding fragments, rather than whole antibodies. Smaller fragment sizes allow for rapid clearance, and may lead to improved access to solid tumors.

Various techniques have been developed for the production of antibody fragments. Traditionally, these fragments were derived via proteolytic digestion of intact antibodies (see, Morimoto et al., *J. Biochem Biophys. Method.* 24:107-117 (1992); and Brennan et al., *Science* 229:81 (1985)). However, these fragments can now be produced directly by recombinant host cells.

Bispecific and Multispecific Antibodies

Bispecific antibodies (BsAbs) are antibodies that have binding specificities for at least two different epitopes, including those on the same or another protein. Alternatively, one arm can bind the target antigen, and another arm can be combined with an arm that binds a triggering molecule on a leukocyte such as a T-cell receptor molecule (e.g., CD3), or Fe receptors for IgG (FcγR) such as FcγR1 (CD64), FcγRII (CD32) and FcγRIII (CD16), so as to focus and localize cellular defense mechanisms to the target antigen-expressing cell. Bispecific antibodies may also be used to localize cytotoxic agents to cells which express the target antigen. Such antibodies possess one arm that binds the desired antigen and another arm that binds the cytotoxic agent (e.g., saporin, anti-interferon-α, vinca alkaloid, ricin A chain, methotrexate or radioactive isotope hapten).

Methods for making bispecific antibodies are known in the art, including chemical linkage and by recombinant methods. For example, in one approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, $C_H2$, and $C_H3$ regions, DNAs encoding the immunoglobulin heavy chain fusions can be inserted into expression vectors, and expressed in a suitable host organism.

According to another approach described in WO 96/27011 or U.S. Pat. No. 5,731,168, the interface between a pair of antibody molecules can be engineered to maximize the percentage of heterodimers which are recovered from recombinant cell culture. The preferred interface comprises at least a part of the $C_H3$ region of an antibody constant domain. In this method, one or more small amino acid side chains from the interface of the first antibody molecule are replaced with larger side chains (e.g., tyrosine or tryptophan). Compensatory "cavities" of identical or similar size to the large side chains(s) are created on the interface of the second antibody molecule by replacing large amino acid side chains with smaller ones (e.g., alanine or threonine). This provides a mechanism for increasing the yield of the heterodimer over other unwanted end-products such as homodimers.

Various techniques for making and isolating bivalent antibody fragments directly from recombinant cell culture have also been described. For example, bivalent heterodimers have been produced using leucine zippers. Kostelny et al., *J. Immunol.*, 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. In some embodiments, two VH domains from different HcAbs are genetically fused to each other to provide bispecific antibodies.

Antibodies with more than two valencies are contemplated. For example, trispecific antibodies can be prepared. Tutt et al., *J. Immunol.* 147: 60 (1991).

HcAb Conjugates

In some embodiments, the HcAb isolated from the genetically modified non-human animal is conjugated to a label and/or a cytotoxic agent. As used herein, a label is a moiety that facilitates detection of the antibody and/or facilitates detection of a molecule to which the antibody binds. Nonlimiting exemplary labels include, but are not limited to, radioisotopes, fluorescent groups, enzymatic groups, chemiluminescent groups, biotin, epitope tags, metal-binding tags, etc. One skilled in the art can select a suitable label according to the intended application.

As used herein, a cytotoxic agent is a moiety that reduces the proliferative capacity of one or more cells. A cell has reduced proliferative capacity when the cell becomes less able to proliferate, for example, because the cell undergoes apoptosis or otherwise dies, the cell fails to proceed through the cell cycle and/or fails to divide, the cell differentiates, etc. Nonlimiting exemplary cytotoxic agents include, but are not limited to, radioisotopes, toxins, and chemotherapeutic agents. One skilled in the art can select a suitable cytotoxic according to the intended application.

In some embodiments, a label and/or a cytotoxic agent is conjugated to an antibody using chemical methods in vitro. Nonlimiting exemplary chemical methods of conjugation are known in the art, and include services, methods and/or reagents commercially available from, e.g., Thermo Scientific Life Science Research Produces (formerly Pierce Rockford, Ill.), Prozyme (Hayward, Calif.), SACRI Antibody Services (Calgary, Canada), AbD Serotec (Raleigh, N.C.), etc. In some embodiments, when a label and/or cytotoxic agent is a polypeptide, the label and/or cytotoxic agent can be expressed from the same expression vector with at least one antibody chain to produce a polypeptide comprising the label and/or cytotoxic agent fused to an antibody chain. One skilled in the art can select a suitable method for conjugating a label and/or cytotoxic agent to an antibody according to the intended application.

Other Amino Acid Sequence Modifications

In some embodiments, modifications to the amino acid sequence of the HcAb isolated from the genetically modified non-human animal are contemplated. For example, it may be desirable to improve the binding affinity and/or other biological properties of the antibody. Amino acid sequence variants of the antibody are prepared by introducing appropriate nucleotide changes into the antibody nucleic acid, or by peptide synthesis. Such modifications include, for example, deletions from, and/or insertions into and/or substitutions of, residues within the amino acid sequences of the antibody. Any combination of deletion, insertion, and substitution is made to arrive at the final construct, provided that the final construct possesses the desired characteristics. The amino acid changes also may alter post-translational processes of the antibody, such as changing the number or position of glycosylation sites.

A useful method for identification of certain residues or regions of the antibody that are preferred locations for mutagenesis is called "alanine scanning mutagenesis" as described by Cunningham and Wells in *Science,* 244:1081-1085 (1989). Here, a residue or group of target residues are identified (e.g., charged residues such as arg, asp, his, lys, and glu) and replaced by a neutral or negatively charged amino acid (most preferably alanine or polyalanine) to affect the interaction of the amino acids antigen. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, ala scanning or random mutagenesis is conducted at the target codon or region and the expressed antibody variants are screened for the desired activity.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue or the antibody fused to a cytotoxic polypeptide. Other insertional variants of the antibody molecule include the fusion to the N- or C-terminus of the antibody to an enzyme (e.g. for ADEPT) or a polypeptide which increases the serum half-life of the antibody.

Another type of variant is an amino acid substitution variant. These variants have at least one amino acid residue in the antibody molecule replaced by a different residue. The sites of greatest interest for substitutional mutagenesis include the hypervariable regions, but FR alterations are also contemplated.

EXAMPLES

The examples below are intended to be purely exemplary of the invention and should therefore not be considered to limit the invention in any way. The following examples are offered by way of illustration and not by way of limitation.

Example 1: Heavy Chain-Only Antibody Production by Genetically Modified Mice Exemplary genetically modified mice were produced using CRISPR/Cas9 gene editing technology, which deleted a 7.2 kb endogenous gene fragment encoding Cγ3, Cγ1, Cγ2b and CH1 exon of Cγ2c at the endogenous IgH locus. The genetically modified mice were viable, fertile and had normal B cell development. The genetically modified mice exclusively produced. HcAbs in response to antigen challenges.

CRISPR/Cas9 Mediated Large Deletion in Mouse Genome in Cells

The murine immunoglobulin heavy chain (IgH) locus consists of eight different constant (C) genes, most of which, except Cδ, contain a cytokine-inducible promoter and a highly repetitive switch (S) region. These constant genes are localized downstream of heavy chain variable region and D J regions. The IgG loci were engineered by CRISPR/Cas9 mediated genome deletion (e.g., FIG. 1). A system was first designed to target IgG constant regions of the mouse IgH locus, then CRISPR/Cas9 targeting sequences flanking immediately upstream of the CH1 exon of Cγ constant region and downstream of the CH1 exon of IgG2c were selected. After protospacer adjacent motif (PAM, 5'-NGG (SEQ ID NO: 26)) of *S. pyogenes* Cas9 and candidate gRNAs were selected, the gRNAs were cloned into the vector pX330 to generate pX330-gRNAs, which directed expression of Cas9 and gRNAs in mammalian cells.

Figure 2:
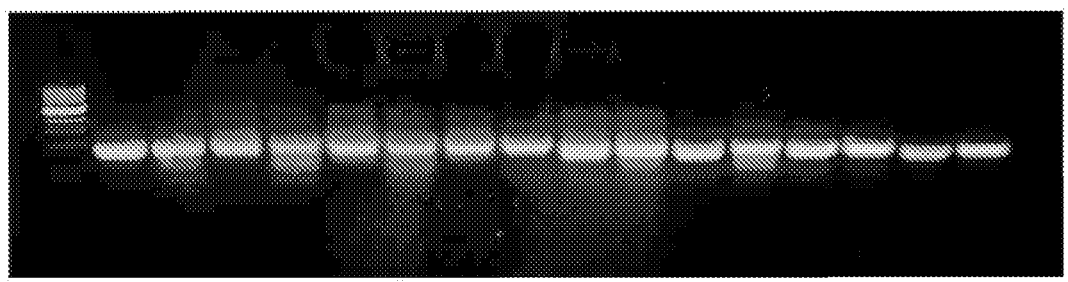
FIG. 2 shows T7E1 assays to determine cleavage efficacy of individual gRNAs. gRNA-1, -2, and -3 target the intron immediately upstream of the CH1 exon of mouse IgH Cγ3 gene and gRNA-4, -5, and -6 target the intron immediately downstream of the CH1 exon of mouse IgH Cγ2c gene.

Mouse neuro2A cells were transfected with pX330-gRNAs, and then the transfected neuro2A cells were collected 48 hours post transfection. The efficiency of each gRNA in Cas9 targeting was measured using the T7E1 assay, which qualitatively measured the frequency of double strand break (DSB) generation as the result of repair through non-homologous end joining (NHEJ). As shown in FIG. 2, variable levels of Cas9 cleavage efficiency were found for the gRNA sites tested. On the basis of their high activity, for subsequent experiments targeting the immunoglobulin loci of WT cells, one pair of gRNAs was selected: one gRNA targeting the intron upstream of the CH1 exon of IgG3, and one gRNA targeting downstream of the CH1 exon of IgG2c.

The selected pair of pX330-gRNAs was co-transfected into neuro2A cells. Genomic nested PCRs were performed with primers designed to flank the deleted region. The size of the expected PCR products confirmed that the constant region of IgG3, IgG1, IgG2b and CH1 exon of IgG2c of the mouse IgH locus, which is 72.7 kb long, was efficiently deleted by the selected pair of Cas9/gRNA in mouse cells.

Efficient Generation of IgH Mutant Mice by Cas9/gRNAs

Following the in vitro analysis of Cas9-mediated genome editing in mouse cell line, the efficiency and specificity of the selected Cas9/gRNAs pair in generating mutant mice were evaluated. Cas9 mRNA was injected into one-cell mouse embryos together with the selected pair of sgRNAs which targeted the first intron upstream of the CH1 exon of IgG3 and the immediate intron downstream of the CH1 exon of IgG2c genomic DNA, a region spanning 72.7 kb.

Figure 3:
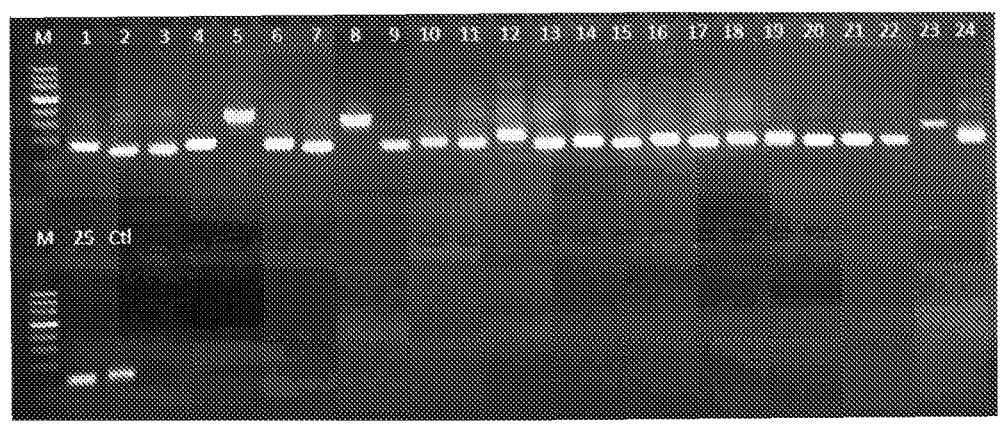
FIG. 3 shows genotyping results of F0 founders of the IgH locus modified mice, which were assayed by PCR. Twenty-five out of 44 F0 mice were genotyped positive for IgH deletions. The genotyping PCR products of the 25 mice with the expected deletions are shown.

As shown in FIG. 3, among 44 F0 pups, 25 thunders, with editing efficiency of 56.8%, was confirmed by PCR genotyping with subsequent sequencing. Of the 25 founder mice, 13 mice were genotyped as having bi-allelic deletion and 12 mice had single-allelic deletion.

To validate the CRISPR editing results by Sanger sequencing, gel-purified nested genotyping PCR products from the 25 genome-modified mice were cloned into pGEM-T Easy vector (Promega, catalog no. A1360) by TA cloning. Plasmid DNAs were submitted for Sanger sequencing to determine the DNA sequences in edited mice. Sequences of the mice are shown in Table 1. The sequencing results showed that in all 25 founders, the region between the targets sites of the pair of sgRNAs, which spans around 72.7 kb, was deleted.

TABLE 1

Sanger sequencing results of genotyping PCR products from 25 genome-modified mice (FIG. 3) confirmed deletion of the 72.7 kb IgH gene fragment.

Mouse #1 (SEQ ID NO: 1)
GCTATATGATGCCCTGACCTAGGTGATATATCCTACATGCTCTCTGTAGAACCCT
GGCATCCTTGTAGGACCAAGGCTGAACTCCTCCAGGTGCCTGAATCCAGCTGTCT
GATAACCTCACTCTAAGGCCTTAGCCTAGCTAGACCAGCCAGGATCAGCAGCCA
TCACCAGGAAAGGGAACTTAGCCCAGAAGAGAAGGAGATACTGCCTCTGACTCC
CTCT TABLE 1-continued Sanger sequencing results of genotyping PCR products from 25 genome-modified mice (FIG. 3) confirmed deletion of the 72.7 kb IgH gene fragment.

Mouse #2 (SEQ ID NO: 2)
GCTATATGATGCCCTGNCCTAGGTGATGTATCCTACATGCTCTTTGCAGAACCCT
GGCATCCTTGTAGGAATAATCACTTAGTTAGCCTAGCTAGACCAGCCAGGATCA
GCAGCCATCACCAGGAAAGGGAACTTAGCCCAGAAGAGAAGGAGATACTGCCT
CTGACTCCCTCT Mouse #3 (SEQ ID NO: 3)
ATATGATGCCCTGACCTAGGTGATATATCCTACATGCTCTTTGCAGAACCCTGGC
ATCCNTGNAGGATCTGAGGCCTTAGACTAGCTAGACCAGCCAGGATCAGCAGCC
ATCATCAGGAAAGGGAACTTATCCCCGAGGAAAAGGAAATGCCGCCTCNGACTC
CCT Mouse #4 (SEQ ID NO: 4)
TGCTATATGATGCCCTGACCTAGGTGANATATCCTACATGCTCTTTGCAGAACCCT
GGCATCCTTGTAGGAGGGCTGAACTCCTCCAGGTGCCTGAATCCAGCTGTCTGAT
AACCTCACAAGGCCTTAGCCTAGCTAGACCAGCCAGGATCAGCAGCCATCACCA
GGAAAGGGAACTTAGCCCAGAAGAGAAGGAGATACTGCCTCTGACTCCCTCT Mouse #5 (SEQ ID NO: 5)
GCTATATGATGCCCTGACCTAGGTGATATATCCTACATGCTCTTTGCAGAACCCTG
GCATCCTTGTAGGATTTAAAGCCAAGCTAAGACCAGAGCCTCTCCAAATTTATGA
GGCCACAGATATCAGAAACCCTCACACATCCTCCTTTCTTGCAGCCAAAACAACA
GCCCCNTCGGTCNNTCCACTGNNCCCTGTGTGTGGAGGGGCATCCCCCTCAATCA
TCATAACNT Mouse #6 (SEQ ID NO: 6)
GCTATATGATGCCCNGACCTAGGTGATATATCCTACATGCTCTTTGCAGAACCCN
TGTTCATCNAANGATGITATCAAACAGCTGGATTCAGGCACCTGGAGGAGTTCAG
CCTAGCTAGACCAGCCAGGATCAGCAGCCATCACCAGGAAAGGGAACTTAGCCC
AGAAGAGAAGGAGATACTGCCTCTGACTCCCTCT Mouse #7 (SEQ ID NO: 7)
GCTATATGATGCCCTGACCTAGGTGATATATCCTACATGCTCTTTGCAGAACCCTG
GCATCCTTGTAGCCTAGCTAGACCAGCCAGGATCAGCAGCCATCACCAGGAAAG
GGAACTTAGCCCAGAAGAGAAGGAGATACTGCCTCTGACTCCCTCT Mouse #8 (SEQ ID NO: 8)
GCTATATGATGCCCTGACCTAGGTGATATATCCTACATGCTCTITGCAGAACCCTG
GCATCCTTGTTGACACGGGTTAATTCTCTTTTAATTATAATAGCACTATTTTCCTT
GCCTCTGCTTTCATTGAAGTAAATTAACACCAATGCTCAATICATTCTTACTCCCA
GGTCCTTTCTGGTCTTTCCATCTCTCCTGTACACTACCTTCCACAATCCCCTGCTCA
AACTCTGAGAGTTACCCCACCACTCTTCTGTGGGTCAACTCAGGCTACTTCATGCC
CTCATAGGAGGATTCCCCTCCTGCCTTATATGCTCCCAGCTGATCCTCCAGGTGCC
TGAATCCAGCTGTCTGATAACCTCAGACCAGCCAGGATCAGCAGCCATCACCANG
AAAGGGAACTTAGCCCAGAAGAGAAGGAGATACTGCCTCTGACTCCCTCT Mouse #9 (SEQ ID NO: 9)
GCTATATGATGCCCTGACCTAGGTGATATATCCTACATGCTCTTTGCAGAACCCTG
GCATCCNTGAAAGGNCTTAGCCTAGCTAGACCAGCCAGGATCAGCANANNNNAN
NANNAAAGGGAACTTAGCCCAAAANAGAANGAGATACTGCCTCTGACTCCCTCT Mouse #10 (SEQ ID NO: 10)
GCTATATGATGCCCTGACCTAGGTGATATATCCTACATGCTCTTTGCAGAACCCTG
GGGCTGTTGTTGTAGCTGCAAGATAGGAGGATGAGTGAGGTTATCAGACAGCTG
GATTCAGGCACCTGGAGGAGTTCAGCCTAGCTAGACCAGCCAGGATCAGCAGCC
ATCACCAGGAAAGGGAACTTAGCCCAGAAGAGAAGGAGATACTGCCTCTGACTC
CCTCT Mouse #11 (SEQ ID NO: 11)
GCTATATGATGCCCTGACCTAGGTGATATATCCTACATGCTCTTTGCAGAACCCTG
GCATCCTTGTCTAGACCAGCCAGGATCAGCAGCCATCACCAGGAAAGGGAACTT
AGCCCAGAAGAGAAGGAGATACTGCCTCTGACTCCCTCT Mouse #12 (SEQ ID NO: 12)
GCTATATGATGCCCTGACCTAGGTGATATATCCTACATGCTCTTTGCAGAACCCTG
GCATCCTTGTAGGCCTTAGCCTAGCTAGACCAGCCAGGATCAGCAGCCATCACCA
GGAAAGGGAACTTAGCCCAGAAGAGAAGGAGATACTGCCTCTGACTCCCTCT Mouse #13 (SEQ ID NO: 13)
GCTATATGATGCCCTGACCTAGGTGATATATCCTACATGCTCTTTGCAGAACCCTA
GCTAGACCAGCCAGGATCAGCAGCCATCACCAGGAAAGGGAACTTAGCCCAGAA
GAGAAGGAGATACTGCCTCTGACTCCCTCT Mouse #14 (SEQ ID NO: 14)
CTATATGATGCCCTGACCTAGGTGATATATCCTACATGCTCTTTGCAGAACCCTGG
CATCCTTGTAGGATCTAAGGCCTTAGCCTAGCTAGACCAGCCAGGATCAGCAGCC TABLE 1-continued Sanger sequencing results of genotyping PCR products from 25 genome-modified mice (FIG. 3) confirmed deletion of the 72.7 kb IgH gene fragment.

ATCACCAAAAATGGGAACTTGGCCCAGAAGAGAAGGAGATACTGCCTCTGACTC
CCTCT

Mouse #15 (SEQ ID NO: 15)
GATGCCCTGACCTAGGTGATATATCCTACATGCTCTTTGCAGAACCCTGGCATCCT
TGTAGGATNGCTAGATCAGCCAGGATAGGCAGAGNCNCCATCAGAGANCGTCAN
CACCCNTGGGAACTTGNCCAATGGCNGNAGAANATACTGCCTCNGACTCCGTCG
AATCNCTGGTGAACTCNCGGNAGCCTGCCCGTCGACCATATGGGAGAGCTCC Mouse #16 (SEQ ID NO: 16)
GCTATATGATGCCCTGACCTAGGTGATATATCCTACATGCTCTTTGCAGAACCCTG
GCCTTAGCCTAGCTAGACCAGCCAGGATCAGCAGCCATCACCAGGAAAGGGAAC
TTAGCCCAGAAGAGAAGGAGATACTGCCTCTGACTCCCTCT Mouse #17 (SEQ ID NO: 17)
TATATGATGCCCTGACCTAGGTGATATATCCTACATGCTCTTTGCAGAACCCTGA
GGTTATCAGACAGCTGGATTCAGGCACCTGGAGGAGACCAGCCAGGATCAGCAG
CCATCACCAGGAAAGGGAACTTAGCCCAGAAGAGAAGGAGATACTGCCTCTGAC
TCCCTCT Mouse #18 (SEQ ID NO: 18)
GCTATATGATGCCCTGACCTAGGTGATATATCCTACATGCTCTTTGCAGAACCCTT
AGCCTAGCTAGACCAGCCAGGATCAGCAGCCATCACCAGGAAAGGGAACTTAGC
CCAGAAGAGAAGGAGATACTGCCTCTGACTCCCTCT Mouse #19 (SEQ ID NO: 19)
GCTATATGATGCCCTGACCTAGGTGATATATCCTACATGCTCTTTGCAGAACCCA
GGCATCCTTGTAGCCTAGCTAGACCAGCCAGGATCAGCAGCCATCACCAGGAAA
GGGAACTTAGCCCAGAAGAGAAGGAGATACTGCCTCTGACTCCCTCT Mouse #20 (SEQ ID NO: 20)
GCTATATGATGCCCTGACCTAGGTGATATATCCTACATGCTCTTTGCAGAACCCTG
GCATCCTTAGCCTAGCTAGACCAGCCAGGATCAGCAGCCATCACCAGGAAAGGG
AACTTAGCCCAGAAGAGAAGGAGATACTGCCTCTGACTCCCTCT Mouse #21 (SEQ ID NO: 21)
GCTATATGATGCCCTGACCTAGGTGATATATCCTACATGCTCTTTGCAGAACCCTG
GCATCCTTAGCCTAGCTAGACCAGCCAGGATCAGCAGCCATCACCAGGAAAGGG
AACTTAGCCCAGAAGAGAAGGAGATACTGCCTCTGACTCCCTCT Mouse #22 (SEQ ID NO: 22)
AACTCTANNNCTTAGGGGANAGGGATCAGAATCTGCAGGGGAGCTGGAACAGGT
AAAGATAAAAGGAATGAAGTATCTGTAAGAGAGTAAGAAAGATGGGATTAATGG
GCATCCAGGAAAACCCCAGGAGGTAACCCCAACAGGGATGTCTGGGAGCTCAGG
TCAGACTTGCATCAAAAGCACAGGGGAAGGATAGGTGGTAGAAGGGTTCCAATC
CATCCTGCTAGACCAGCCAGGATCAGCAGCCAACACCAGGAAAGGGAACTTAGC
CCAGAAGAGAAGGAGATACTGCCTCTGACTCCCTCT Mouse #23 (SEQ ID NO: 23)
GCTATATGATGCCCTGACCTAGGTGANATATCCTACATGCTCTTTGCAGAACCCT
GGCATCCTTGTAGGATCTAAGGCCTTAGCCTAGCTAGACCAGCCAGGATCAGCAG
CCATCACCAGGAAAGGGAACTTAGCCCAGAAGAGAAGGAGATACTGCCTCTGAC
TCCCTCT Mouse #24 (SEQ ID NO: 24)
GCTATATGATGCCCTGACCTAGGTGATATATCCTACATGCTCTTTGCAGAACCCTG
GCATCCTTGTAGGCCTAGCTAGACCAGCCAGGATCAGCAGCCATCACCAGGAAA
GGGAACTTAGCCCAGAAGAGAAGGAGATACTGCCTCTGACTCCCTCT Mouse #25 (SEQ ID NO: 25)
GCTATATGATGCCCTGACCTAGGTGATATATCCTACATGCTCTTTGAGAACCCTG
GCATCCTTGTAGGATCTAAGGCMAGCCTAGCTAGACCAGCCAGGATCAGCAGC
CATCACCAGGAAAGGGAACTTAGCCCAGAAGAGAAGGAGATACTGCCTCTGACT
CCCTCT Heavy-Chain Only IgG Production in IgH Mutant Mice Sera from IgH mutant mice were collected by vein tail bleeding. The presence of heavy chain IgGs was tested by Western blotting analysis using HRP-conjugated goat anti-IgG Subclass 2c specific antibody (Jackson ImmunoResearch Laboratories, catalog no. 115-035-208).

Figure 4:
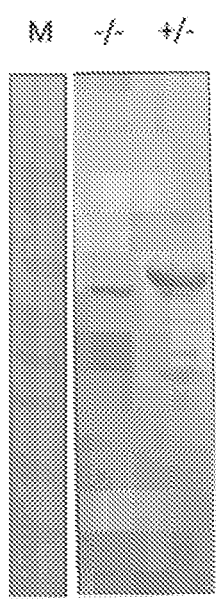
FIG. 4 shows Western blot images from a reducing SDS-PAGE eel of mouse sera from single allelic (+/−) and double allelic (−/−) IgH deletion mice. The gel was blotted with an HRP-conjugated anti-mouse IgG.

As shown in FIG. 4, soluble heavy-chain-only IgG proteins of reduced molecular weight were detected in the plasma of 10-week-old IgH mutant mice. These data suggests that deletion of all CH1 domains of the constant region enables the immunoglobulin heavy chain to be secreted in the absence of the light chain. Furthermore, the heavy chain by itself is enough to support B-cell development and maturation in the IgH mutant mice. These IgG locus modified mice allowed efficient production of antigen-specific IgG heavy chain only antibodies for biomedical research and therapeutic applications.

IgH Mutant Mice has Normal B Cell Development

Figure 5:
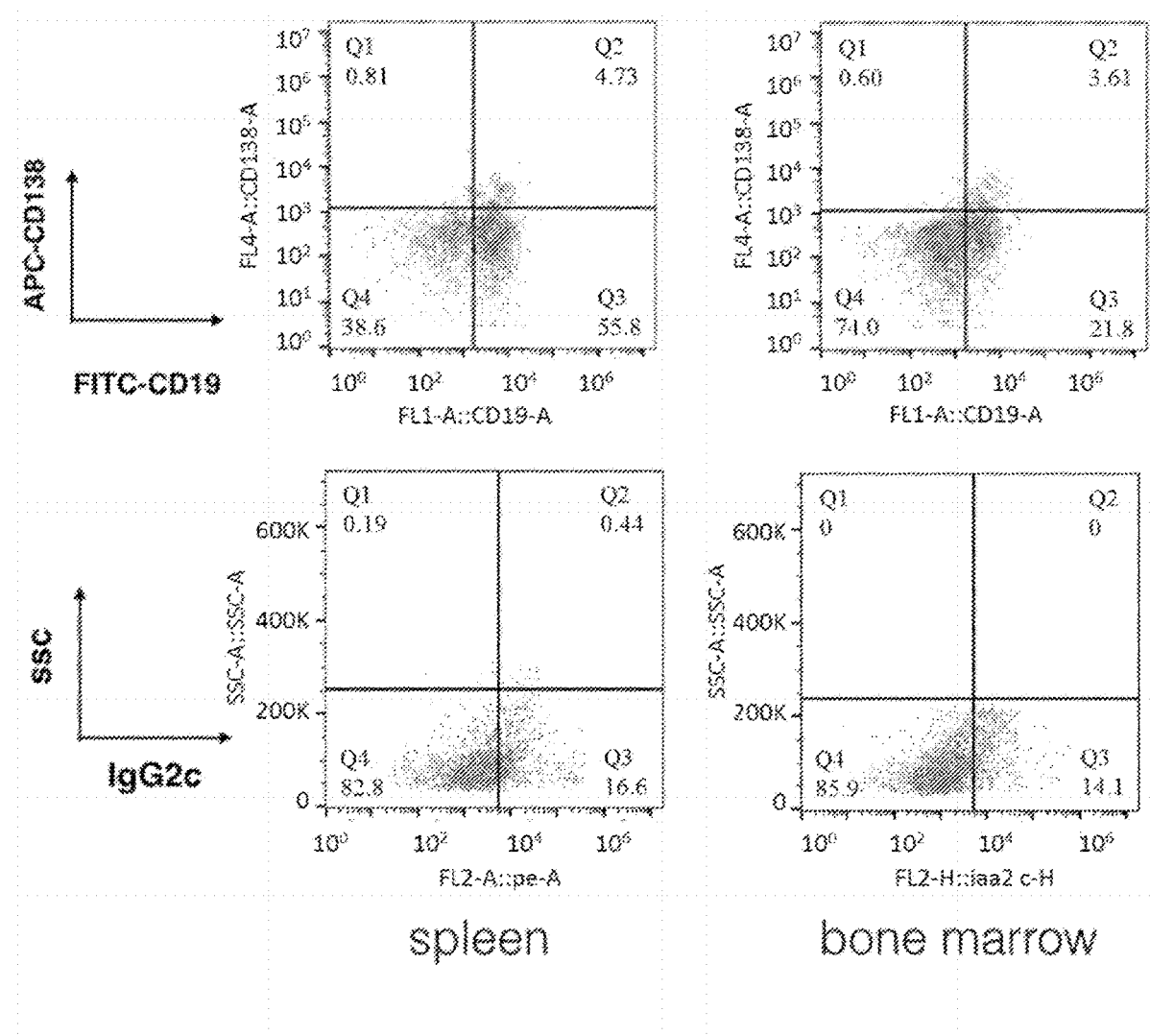
FIG. 5 shows flow cytometry analysis results of cell samples from spleen and bone marrow of genetically modified mice.

The B cell development in genetically modified mice was assessed by flow cytometry analysis. Cell samples from spleen and bone marrow of the genetically modified mice were analyzed using B cell maker CD19 and plasma cell marker CD138. As shown in FIG. 5, B cells that expressed heavy chain only IgG2c molecules were detected in both spleen and bone marrow samples, indicating normal proliferation, differentiation and maturation of B cells and plasma cells in the genetically modified animals.

Robust Immune Response Against Antigen Challenge and Production of High-Affinity Heavy Chain-Only Antibodies Against Immune Checkpoint Molecules The genetically modified mice were immunized with recombinant human PD-1, and HEK293T cells overexpressing full length human PD-1, together with adjuvant on day 1, and boosted on day 14, day 21, and day 28. Serum samples were collected 14, 21, and 31 days after the first immunization. Titer and affinity of PD-1 specific heavy chain-only antibodies in the immunized animals were determined using BLI technology (OctetRed 96) and Biotinylated-human PD-1 coated streptavidin sensors (ForteBio). As shown in FIGS. 6A-6D, very high-affinity heavy chain-only antibodies against human PD-1 were generated 14 days (FIG. 6A, Kd=1.33 nM) after the first immunization. The affinity of the antibodies continued to increase to 50 pmol on day 21 (FIG. 6B) and <1 pmol on day 31 (FIG. 6C).

Discussion

The genome-modified mice described in this example produced heavy chain-only antibodies, which have great potential applications in developing therapeutic antibodies, chimeric antigen receptors (CAR), and T Cell Receptor-like (TCR-L) binders for immune cell therapy. Cytoplasmic injection of Cas9 mRNA and an optimized pair of gRNAs into fertilized oocytes at one cell stage generated endogenous IgH locus-modified mice. In these exemplary mice, all IgG constant region exons were knocked out, except for IgG2c CH2 CH3 in the IgH locus and IgM IgD IgA and IgE locus. Such mice generated IgG2c Heavy Chain only Antibody (HcAb) after immunization challenges.

Camelids (dromedaries, camels, and llamas) and some fish such as sharks produce heavy chain only antibodies (HcAb) naturally in addition to conventional antibodies. These HcAb, lacking CH1 domain, are produced because of a mutation in the CH1 splicing site, leading to the splicing out of CH1 exon in IgG mRNAs, Mice lacking functional light chain genes secret HcAbs despite compromised B cell development. Transgenic mice with an engineered camelid or human IgH transgenic fragment lacking functional CH1 have previously been generated to produce HcAbs in mice. However, these transgenic animals have the following shortcomings: 1) compromised B cell development due to deletion of IgM or Ig L chain locus; 2) limited VH repertoire; and/or 3) mixture of both conventional IgGs and HcAb.

The genetically modified mice described in this example overcome all of these limitations, thus allows in vivo generation of affinity-matured, pure heavy-chain only IgGs at the highest abundance, and using the full mouse endogenous VH repertoire. Advantages of the genetically modified mice described herein include, but are not limited to:

1. The entire constant region exons of IgG isotypes IgG1, IgG3, IgG2b and CH1 exon of IgG2c, spanning a 72.7 kb region of mouse IgH locus was genetically deleted in these mice, leaving IgG2c with intact exons for CH2 and CH3. These mice generated purely affinity-matured Heavy Chain Only IgGs, without any contamination of conventional IgGs.

2. The genetically modified mice described herein have normal B lymphocyte development and maturation, normal V-D-J recombination, normal classic switch recombination (CSR), and normal somatic hypermutations. In these mice, genome modification was made only in the constant regions of the IgG loci, while all other regions including the full IgVH repertoire, mouse D and J regions, all constant domain exons of IgM, IgD, IgA, IgE, as well as L chain locus and mouse IgH regulatory (genome sequence were kept intact.

3. The genetically modified mice described herein expressed a full repertoire of mouse heavy chain variable domains. Since the IgH V locus contains 2.5-fold more functional V genes than the entire human IgH V locus (110 vs 44), the mice described herein are capable of generating more diversified antibody repertoire than any other human IgH transgenic mice.

Example 2: Genetically Modified Rats for Production of Heavy Chain Only Antibodies Exemplary genetically modified rats are produced using CRISPR/Cas9 gene editing technology, which deletes a 140 kb endogenous gene fragment encoding Cγ2c, Cγ2a, Cγ1 and CH1 exon of Cγ2b at the endogenous IgH locus. The genetically modified rats are viable, fertile and have normal B cell development. The genetically modified rats exclusively produce HcAbs in response to antigen challenges.

CRISPR/Cas9 Mediated Large Deletion in Rat Genome in Cells

Figure 7:
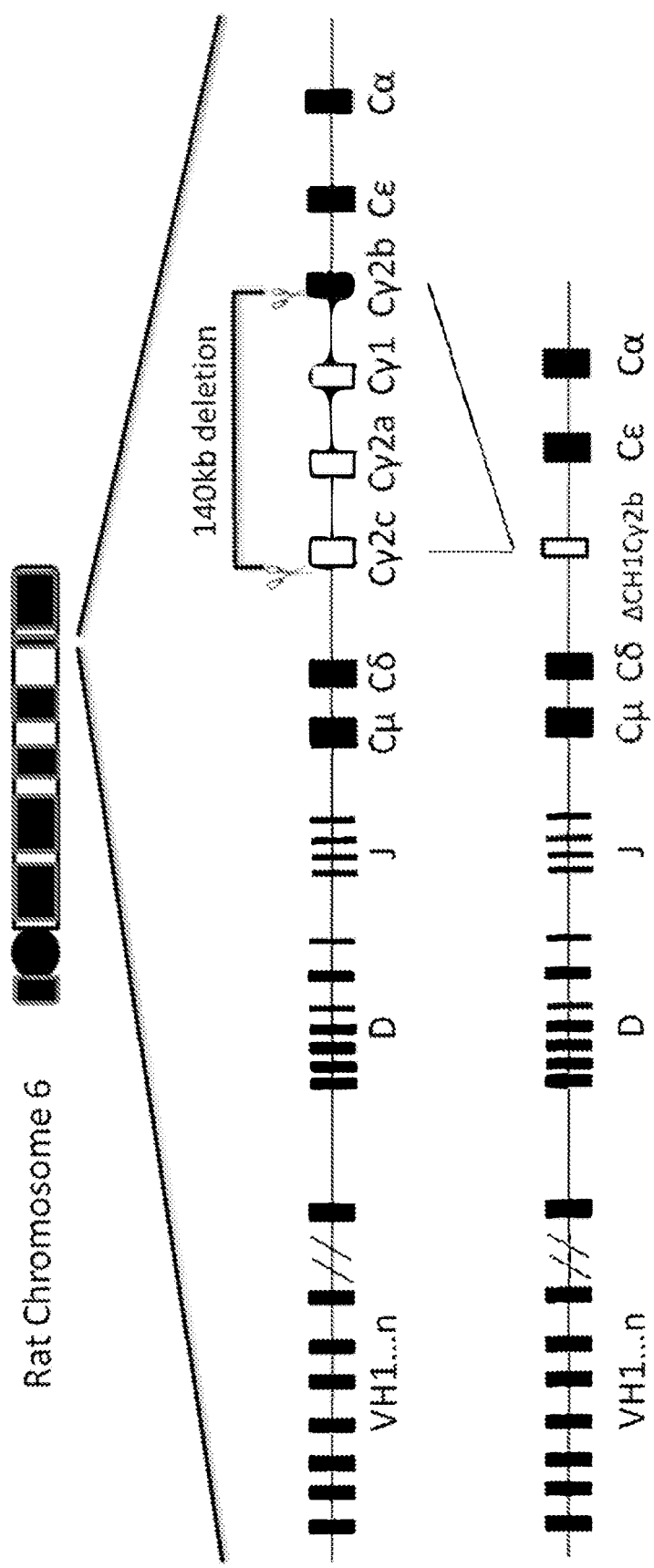
FIG. 7 shows rat IgH locus.

The IgG loci in the rat (genome are engineered using CRISPR/Cas9 mediated genome deletion (e.g., FIG. 7). A system is first designed to target IgG constant regions of the rat IgH locus, then CRISPR/Cas9 targeting sequences flanking immediately upstream of the CH1 exon of Cγ2c constant region and downstream of the CH1 exon of IgG2b are selected. After protospacer adjacent motif (PAM, 5'-NGG (SEQ ID NO: 26)) of S. pyogenes Cas9 and candidate gRNAs are selected, the gRNAs are cloned into the vector pX330 to generate pX330-gRNAs, which directs expression of Cas9 and gRNAs in rat cells.

The rat immunoglobulin heavy chain (IgH) locus consists of eight different constant (C) genes, most of which, except Cδ, contain a cytokine-inducible promoter and a highly repetitive switch (S) region. These constant genes are localized downstream of heavy chain variable region and D J regions. Rat fibroblast cells are transfected with pX330-gRNAs, and then the transfected fibroblast cells are collected 48 hours post transfection. The efficiency of each gRNA in Cas9 targeting is measured using the T7E1 assay, which qualitatively measures the frequency of double strand break (DSB) generation as the result of repair through non-homologous end joining (NHEJ). Variable levels of Cas9 cleavage efficiency are found for the gRNA sites tested. On the basis of their high activity, for subsequent experiments targeting the immunoglobulin loci of WT cells, one pair of gRNAs is selected: one gRNA targeting the intron upstream of the CH1 exon of Cγ2c, and one gRNA targeting downstream of the CH1 exon of Cγ2b.

The selected pair of pX330-gRNAs is co-transfected into rat fibroblast cells. Genomic nested PCRs are performed with primers designed to flank the deleted region. The size of the expected PCR products confirms that the constant region of Cγ2c, Cγ2a Cγ1, and CH1 exon of Cγ2c of the rat IgH locus, which is 140 kb long, is efficiently deleted by the selected pair of Cas9/gRNA in rat cells.

Efficient Generation of IgH Mutant Rats by Cas9/gRNAs

Following the in vitro analysis of Cas9-mediated genome editing in rat cell line, the efficiency and specificity of the selected Cas9/gRNAs pair in generating mutant rat are evaluated. Cas9 mRNA is injected into one-cell rat embryos together with the selected pair of sgRNAs which target the first intron upstream of the CH1 exon of Cγ2c and the immediate intron downstream of the CH1 exon of Cγ2b genomic DNA, a region spanning 140 kb.

F0 pups are genotyped with PCR and founders with the expected 140 kb deletion are confirmed by PCR genotyping with subsequent Sanger sequencing.

Example 3: Genetically Modified Rabbits for Production of Heavy Chain Only Antibodies Exemplary genetically modified rabbits are produced using CRISPR/Cas9 gene editing technology, which deletes a CH1 exon (Accession number: AY386696; nucleotide 55580-555868) of Cγ at the endogenous IgH locus The genetically modified rabbits are viable, fertile and have normal B cell development. The genetically modified rabbits exclusively produce HcAbs in response to antigen challenges.

CRISPR/Cas9 Mediated Large Deletion in Rabbit Genome in Cells

Figure 8:
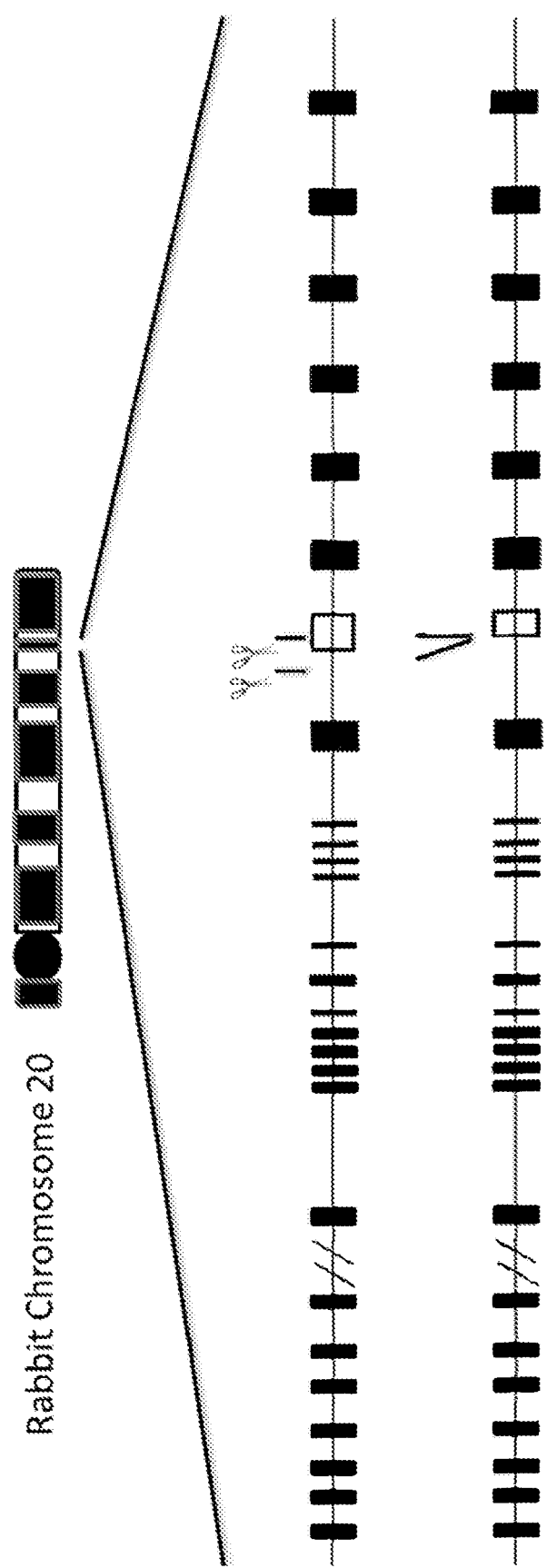
FIG. 8 shows rabbit IgH locus.

The rabbit immunoglobulin heavy chain (IgH) locus consists of 17 different constant (C) genes, including Cμ, Cε, 13 Cα, but only one Cγ. These constant genes are localized downstream of heavy chain variable region and D J regions. The Cγ loci are engineered by CRISPR/Cas9 mediated genome deletion (e.g., FIG. 8). A system is first designed to target Cγ constant region of the rabbit IgH locus, then CRISPR/Cas9 targeting sequences flanking immediately upstream of the CH1 exon of Cγ constant region and downstream of the CH1 exon of Cγ are selected. After protospacer adjacent motif and candidate gRNAs are selected, the gRNAs are cloned into the vector pX330 to generate pX330-gRNAs, which directs expression of Cas9 and gRNAs in rabbit cells.

Rabbit fibroblast cells are transfected with pX330-gRNAs, and then the transfected fibroblast cells are collected 48 hours post transfection. The efficiency of each gRNA in Cas9 targeting is measured using the T7E1 assay, which qualitatively measures the frequency of double strand break (DSB) generation as the result of repair through non-homologous end joining (NHEJ). Variable levels of Cas9 cleavage efficiency are found for the gRNA sites tested. On the basis of their high activity, for subsequent experiments targeting the immunoglobulin loci of WT cells, one pair of gRNAs is selected: one gRNA targeting the intron upstream of the CH1 exon of Cγ and one gRNA targeting downstream of the CH1 exon of Cγ.

The selected pair of pX330-gRNAs is co-transfected into rabbit fibroblast cells. Genomic nested PCRs are performed with primers designed to flank the deleted region. The size of the expected PCR products confirms that the CH1 exon of Cγ of the rabbit IgH locus is efficiently deleted by the selected pair of Cas9/gRNA in rabbit cells.

Efficient Generation of IgH Mutant Rabbits by Cas9/gRNAs

Following the in vitro analysis of Cas9-mediated genome editing in rabbit cell line, the efficiency and specificity of the selected Cas9/gRNAs pair in generating mutant rabbit are evaluated. Cas9 mRNA is injected into one-cell rabbit embryos together with the selected pair of sgRNAs which target the first intron upstream of the CH1 exon of Cγ and the immediate intron downstream of the CH1 exon (about 288 nt) of Cγ genomic DNA.

F0 pups are genotyped with PCR and founders with the expected CH1 exon deletion are confirmed by PCR genotyping with subsequent Sanger sequencing.

The disclosures of all publications, patents, patent applications and published patent applications referred to herein are hereby incorporated herein by reference in their entirety.

What is claimed is:

1. A method of producing a heavy chain-only antibody (HcAb) that specifically binds to an antigen of interest, comprising:
   (a) immunizing a genetically modified non-human animal with the antigen, wherein the genetically modified non-human animal comprises a germline genome comprising an engineered immunoglobulin heavy chain (IgH) allele at an endogenous IgH locus, wherein the engineered IgH allele lacks endogenous gene segments encoding functional CH1 domains of all endogenous IgG subclasses, wherein the genetically modified non-human animal is a mouse or a rat, and wherein the engineered IgH allele lacks an endogenous gene segment comprising Cγ3, Cγ1, Cγ2b and CH1 exon of Cγ2c; and
   (b) obtaining a HcAb that specifically binds to the antigen from the immunized genetically modified non-human animal, thereby producing the HcAb.

2. The method of claim 1, wherein step (b) comprises:
   (i) obtaining a cell comprising a nucleic acid encoding the heavy chain of the HcAb;
   (ii) obtaining the nucleic acid from the cell; and
   (iii) expressing the nucleic acid in a host cell to provide the HcAb.

3. The method of claim 1, further comprising affinity maturation of the HcAb.

4. A B cell isolated from a genetically modified non-human animal, wherein the genetically modified non-human animal comprises a germline genome comprising an engineered immunoglobulin heavy chain (IgH) allele at an endogenous IgH locus, wherein the engineered IgH allele lacks endogenous gene segments encoding functional CH1 domains of all endogenous IgG subclasses, wherein the genetically modified non-human animal is a mouse or a rat, and wherein the engineered IgH allele lacks an endogenous gene segment comprising Cγ3, Cγ1, Cγ2b and CH1 exon of Cγ2c.

5. The method of claim 1, wherein:
   (i) the genetically modified non-human animal does not express IgG molecules comprising light chains;
   (ii) the genetically modified non-human animal is fertile; and/or
   (iii) the genetically modified non-human animal has substantially normal B-cell development and maturation.

6. The method of claim 1, wherein the genetically modified non-human animal is a mouse.

7. The method of claim 6, wherein the endogenous gene segment is about 72.7 kb long.

8. The method of claim 7, wherein the engineered IgH allele comprises a nucleotide sequence comprising SEQ ID NO: 27 and SEQ ID NO: 28.

9. The method of claim 7, wherein the engineered IgH allele comprises a nucleotide sequence selected from SEQ ID NOs: 1-25.

10. The method of claim 1, wherein the genetically modified non-human animal is a rat.

11. A hybridoma produced based on the B cell of claim 4.

* * * * *

SEQUENCE LISTING

```
<160> NUMBER OF SEQ ID NOS: 28

<210> SEQ ID NO 1
<211> LENGTH: 222
<212> TYPE: DNA
<213> ORGANISM: Artificial Sequence
<220> FEATURE:
<223> OTHER INFORMATION: Synthetic Construct

<400> SEQUENCE: 1
gctatatgat gccctgacct aggtgatata tcctacatgc tctctgtaga accctggcat      60
ccttgtagga ccaaggctga actcctccag gtgcctgaat ccagctgtct gataacctca    120
ctctaaggcc ttagcctagc tagaccagcc aggatcagca gccatcacca ggaaagggaa    180
cttagcccag aagagaagga gatactgcct ctgactccct ct                       222

<210> SEQ ID NO 2
<211> LENGTH: 174
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 17
<223> OTHER INFORMATION: n = A,T,C or G
```

<400> SEQUENCE: 2
gctatatgat gccctgncct aggtgatgta tcctacatgc tctttgcaga accctggcat    60
ccttgtagga ataatcactt agttagccta gctagaccag ccaggatcag cagccatcac   120
caggaaaggg aacttagccc agaagagaag gagatactgc ctctgactcc ctct         174

<210> SEQ ID NO 3
<211> LENGTH: 166
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 60, 63, 158
<223> OTHER INFORMATION: n = A,T,C or G

<400> SEQUENCE: 3
atatgatgcc ctgacctagg tgatatatcc tacatgctct ttgcagaacc ctggcatccn    60
tgnaggatct gaggccttag actagctaga ccagccagga tcagcagcca tcatcaggaa   120
agggaactta tccccgagga aaaggaaatg ccgcctcnga ctccct                  166

<210> SEQ ID NO 4
<211> LENGTH: 217
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 28
<223> OTHER INFORMATION: n = A,T,C or G

<400> SEQUENCE: 4
tgctatatga tgccctgacc taggtganat atcctacatg ctctttgcag aaccctggca    60
tccttgtagg agggctgaac tcctccaggt gcctgaatcc agctgtctga taacctcaca   120
aggccttagc ctagctagac cagccaggat cagcagccat caccaggaaa gggaacttag   180
cccagaagag aaggagatac tgcctctgac tccctct                            217

<210> SEQ ID NO 5
<211> LENGTH: 230
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 172, 179, 180, 188, 189, 229
<223> OTHER INFORMATION: n = A,T,C or G

<400> SEQUENCE: 5
gctatatgat gccctgacct aggtgatata tcctacatgc tctttgcaga accctggcat    60
ccttgtagga tttaaagcca agctaagacc agagcctctc caaatttatg aggccacaga   120
tatcagaaac cctcacacat cctcctttct tgcagccaaa acaacagccc cntcggtcnn   180
tccactgnnc cctgtgtgtg gagggcatc cccctcaatc atcataacnt               230

<210> SEQ ID NO 6
<211> LENGTH: 198
<212> TYPE: DNA
<213> ORGANISM: Artificial Sequence
<220> FEATURE:
<223> OTHER INFORMATION: Synthetic Construct

```
<220> FEATURE:
<221> NAME/KEY: misc_feature
<222> LOCATION: 15, 55, 64, 67
<223> OTHER INFORMATION: n = A,T,C or G

<400> SEQUENCE: 6
gctatatgat gcccngacct aggtgatata tcctacatgc tctttgcaga acccntgttc       60
atcnaangat gttatcaaac agctggattc aggcacctgg aggagttcag cctagctaga      120
ccagccagga tcagcagcca tcaccaggaa agggaactta gcccagaaga aaggagata      180 ctgcctctga ctccctct                                                    198

<210> SEQ ID NO 7
<211> LENGTH: 156
<212> TYPE: DNA
<213> ORGANISM: Artificial Sequence
<220> FEATURE:
<223> OTHER INFORMATION: Synthetic Construct

<400> SEQUENCE: 7
gctatatgat gccctgacct aggtgatata tcctacatgc tctttgcaga accctggcat       60
ccttgtagcc tagctagacc agccaggatc agcagccatc accaggaaag gaacttagc      120 ccagaagaga aggagatact gcctctgact ccctct                                156

<210> SEQ ID NO 8
<211> LENGTH: 442
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 391
<223> OTHER INFORMATION: n = A,T,C or G

<400> SEQUENCE: 8
gctatatgat gccctgacct aggtgatata tcctacatgc tctttgcaga accctggcat       60
ccttgttgac acgggttaat tctcttttaa ttataatagc actattttcc ttgcctctgc      120
tttcattgaa gtaaattaac accaatgctc aattcattct tactcccagg tccttttctgg    180 tctttccatc tctcctgtac actaccttcc acaatcccct gctcaaactc tgagagttac     240
cccaccactc ttctgtgggt caactcaggc tacttcatgc cctcatagga ggattcccct    300
cctgccttat atgctcccag ctgatcctcc aggtgcctga atccagctgt ctgataacct    360
cagaccagcc aggatcagca gccatcacca ngaaagggaa cttagcccag aagagaagga    420
gatactgcct ctgactccct ct                                              442

<210> SEQ ID NO 9
<211> LENGTH: 164
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 63, 71, 103, 105, 106, 107, 108, 110, 111, 113, 114,
      135, 140
<223> OTHER INFORMATION: n = A,T,C or G

<400> SEQUENCE: 9
gctatatgat gccctgacct aggtgatata tcctacatgc tctttgcaga accctggcat       60
ccntgaaagg ncttagccta gctagaccag ccaggatcag canannnnan nannaaaggg     120
```
aacttagccc aaaanagaan gagatactgc ctctgactcc ctct         164

<210> SEQ ID NO 10
<211> LENGTH: 223
<212> TYPE: DNA
<213> ORGANISM: Artificial Sequence
<220> FEATURE:
<223> OTHER INFORMATION: Synthetic Construct

<400> SEQUENCE: 10
gctatatgat gccctgacct aggtgatata tcctacatgc tctttgcaga accctggggc    60
tgttgttgta gctgcaagat aggaggatga gtgaggttat cagacagctg gattcaggca   120
cctggaggag ttcagcctag ctagaccagc caggatcagc agccatcacc aggaaaggga   180
acttagccca gaagagaagg agatactgcc tctgactccc tct                     223

<210> SEQ ID NO 11
<211> LENGTH: 149
<212> TYPE: DNA
<213> ORGANISM: Artificial Sequence
<220> FEATURE:
<223> OTHER INFORMATION: Synthetic Construct

<400> SEQUENCE: 11
gctatatgat gccctgacct aggtgatata tcctacatgc tctttgcaga accctggcat    60
ccttgtctag accagccagg atcagcagcc atcaccagga aagggaactt agcccagaag   120
agaaggagat actgcctctg actccctct                                     149

<210> SEQ ID NO 12
<211> LENGTH: 163
<212> TYPE: DNA
<213> ORGANISM: Artificial Sequence
<220> FEATURE:
<223> OTHER INFORMATION: Synthetic Construct

<400> SEQUENCE: 12
gctatatgat gccctgacct aggtgatata tcctacatgc tctttgcaga accctggcat    60
ccttgtaggc cttagcctag ctagaccagc caggatcagc agccatcacc aggaaaggga   120
acttagccca gaagagaagg agatactgcc tctgactccc tct                     163

<210> SEQ ID NO 13
<211> LENGTH: 140
<212> TYPE: DNA
<213> ORGANISM: Artificial Sequence
<220> FEATURE:
<223> OTHER INFORMATION: Synthetic Construct

<400> SEQUENCE: 13
gctatatgat gccctgacct aggtgatata tcctacatgc tctttgcaga accctagcta    60
gaccagccag gatcagcagc catcaccagg aaagggaact agcccagaa gagaaggaga   120 tactgcctct gactccctct                                               140

<210> SEQ ID NO 14
<211> LENGTH: 170
<212> TYPE: DNA
<213> ORGANISM: Artificial Sequence
<220> FEATURE:
<223> OTHER INFORMATION: Synthetic Construct

<400> SEQUENCE: 14
ctatatgatg cccctgaccta ggtgatatat cctacatgct ctttgcagaa ccctggcatc    60
cttgtaggat ctaaggcctt agcctagcta gaccagccag gatcagcagc catcaccaaa   120
aatgggaact tggcccagaa gagaaggaga tactgcctct gactccctct             170

<210> SEQ ID NO 15
<211> LENGTH: 216
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 65, 91, 93, 104, 110, 116, 127, 136, 138, 143, 154, 169,
      181, 185
<223> OTHER INFORMATION: n = A,T,C or G

<400> SEQUENCE: 15
gatgccctga cctaggtgat atatcctaca tgctctttgc agaaccctgg catccttgta    60
ggatngctag atcagccagg ataggcagag ncnccatcag agancgtcan cacccntggg   120
aacttgncca atggcngnag aanatactgc ctcngactcc gtcgaatcnc tggtgaactc   180
ncggnagcct gcccgtcgac catatgggag agctcc                             216

<210> SEQ ID NO 16
<211> LENGTH: 151
<212> TYPE: DNA
<213> ORGANISM: Artificial Sequence
<220> FEATURE:
<223> OTHER INFORMATION: Synthetic Construct

<400> SEQUENCE: 16
gctatatgat gccctgacct aggtgatata tcctacatgc tctttgcaga accctggcct    60
tagcctagct agaccagcca ggatcagcag ccatcaccag gaaagggaac ttagcccaga   120
agagaaggag atactgcctc tgactccctc t                                 151

<210> SEQ ID NO 17
<211> LENGTH: 170
<212> TYPE: DNA
<213> ORGANISM: Artificial Sequence
<220> FEATURE:
<223> OTHER INFORMATION: Synthetic Construct

<400> SEQUENCE: 17
tatatgatgc cctgacctag gtgatatatc ctacatgctc tttgcagaac cctgaggtta    60
tcagacagct ggattcaggc acctggagga gaccagccag gatcagcagc catcaccagg   120
aaagggaact tagcccagaa gagaaggaga tactgcctct gactccctct             170

<210> SEQ ID NO 18
<211> LENGTH: 146
<212> TYPE: DNA
<213> ORGANISM: Artificial Sequence
<220> FEATURE:
<223> OTHER INFORMATION: Synthetic Construct

<400> SEQUENCE: 18
gctatatgat gccctgacct aggtgatata tcctacatgc tctttgcaga acccttagcc    60
tagctagacc agccaggatc agcagccatc accaggaaag gaacttagc ccagaagaga   120 aggagatact gcctctgact ccctct                                       146

<210> SEQ ID NO 19

<211> LENGTH: 156
<212> TYPE: DNA
<213> ORGANISM: Artificial Sequence
<220> FEATURE:
<223> OTHER INFORMATION: Synthetic Construct

<400> SEQUENCE: 19

```
gctatatgat gccctgacct aggtgatata tcctacatgc tctttgcaga acccaggcat      60
ccttgtagcc tagctagacc agccaggatc agcagccatc accaggaaag ggaacttagc     120
ccagaagaga aggagatact gcctctgact ccctct                                156
```

<210> SEQ ID NO 20
<211> LENGTH: 154
<212> TYPE: DNA
<213> ORGANISM: Artificial Sequence
<220> FEATURE:
<223> OTHER INFORMATION: Synthetic Construct

<400> SEQUENCE: 20

```
gctatatgat gccctgacct aggtgatata tcctacatgc tctttgcaga accctggcat      60
ccttagccta gctagaccag ccaggatcag cagccatcac caggaaaggg aacttagccc     120
agaagagaag gagatactgc ctctgactcc ctct                                  154
```

<210> SEQ ID NO 21
<211> LENGTH: 154
<212> TYPE: DNA
<213> ORGANISM: Artificial Sequence
<220> FEATURE:
<223> OTHER INFORMATION: Synthetic Construct

<400> SEQUENCE: 21

```
gctatatgat gccctgacct aggtgatata tcctacatgc tctttgcaga accctggcat      60
ccttagccta gctagaccag ccaggatcag cagccatcac caggaaaggg aacttagccc     120
agaagagaag gagatactgc ctctgactcc ctct                                  154
```

<210> SEQ ID NO 22
<211> LENGTH: 306
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 8, 9, 10, 20
<223> OTHER INFORMATION: n = A,T,C or G

<400> SEQUENCE: 22

```
aactctannn cttaggggan agggatcaga atctgcaggg gagctggaac aggtaaagat      60
aaaaggaatg aagtatctgt aagagagtaa gaaagatggg attaatgggc atccaggaaa     120
accccaggag gtaaccccaa cagggatgtc tgggagctca ggtcagactt gcatcaaaag     180
cacagggaa ggataggtgg tagaagggtt ccaatccatc ctgctagacc agccaggatc     240
agcagccaac accaggaaag ggaacttagc ccagaagaga aggagatact gcctctgact     300
ccctct                                                                306
```

<210> SEQ ID NO 23
<211> LENGTH: 171
<212> TYPE: DNA
<213> ORGANISM: Artificial Sequence
<220> FEATURE:
<223> OTHER INFORMATION: Synthetic Construct

```
<220> FEATURE:
<221> NAME/KEY: misc_feature
<222> LOCATION: 27
<223> OTHER INFORMATION: n = A,T,C or G

<400> SEQUENCE: 23
gctatatgat gccctgacct aggtganata tcctacatgc tctttgcaga accctggcat      60
ccttgtagga tctaaggcct tagcctagct agaccagcca ggatcagcag ccatcaccag     120
gaaagggaac ttagcccaga agagaaggag atactgcctc tgactccctc t             171

<210> SEQ ID NO 24
<211> LENGTH: 157
<212> TYPE: DNA
<213> ORGANISM: Artificial Sequence
<220> FEATURE:
<223> OTHER INFORMATION: Synthetic Construct

<400> SEQUENCE: 24
gctatatgat gccctgacct aggtgatata tcctacatgc tctttgcaga accctggcat      60
ccttgtaggc ctagctagac cagccaggat cagcagccat caccaggaaa gggaacttag    120
cccagaagag aaggagatac tgcctctgac tccctct                             157

<210> SEQ ID NO 25
<211> LENGTH: 171
<212> TYPE: DNA
<213> ORGANISM: Artificial Sequence
<220> FEATURE:
<223> OTHER INFORMATION: Synthetic Construct

<400> SEQUENCE: 25
gctatatgat gccctgacct aggtgatata tcctacatgc tctttgcaga accctggcat      60
ccttgtagga tctaaggcct tagcctagct agaccagcca ggatcagcag ccatcaccag     120
gaaagggaac ttagcccaga agagaaggag atactgcctc tgactccctc t             171

<210> SEQ ID NO 26
<211> LENGTH: 3
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1
<223> OTHER INFORMATION: n = A,T,C or G

<400> SEQUENCE: 26 ngg                                                                     3

<210> SEQ ID NO 27
<211> LENGTH: 24
<212> TYPE: DNA
<213> ORGANISM: Artificial Sequence
<220> FEATURE:
<223> OTHER INFORMATION: Synthetic Construct

<400> SEQUENCE: 27
tatcctacat gctctttgca gaac                                              24

<210> SEQ ID NO 28
<211> LENGTH: 24
<212> TYPE: DNA
<213> ORGANISM: Artificial Sequence
<220> FEATURE:
```

```
<223> OTHER INFORMATION: Synthetic Construct

<400> SEQUENCE: 28
agaccagcca ggatcagcag ccat                                                 24
```